United States Patent
Okada et al.

Patent Number: 5,055,497
Date of Patent: Oct. 8, 1991

[54] CURABLE RESINOUS COMPOSITION

[75] Inventors: Koichi Okada; Ikuo Omura, both of Kurashiki, Japan

[73] Assignee: Kuraray Company, Ltd., Kurashiki, Japan

[21] Appl. No.: 324,620

[22] Filed: Mar. 17, 1989

[30] Foreign Application Priority Data

Mar. 17, 1988 [JP] Japan .................................. 63-65288

[51] Int. Cl.[5] ........................... C08K 5/49; A61K 6/08
[52] U.S. Cl. .................................... 523/116; 523/115; 524/202; 524/710
[58] Field of Search ................ 523/115, 116; 524/202, 524/710

[56] References Cited

U.S. PATENT DOCUMENTS 4,259,117  3/1981  Yamauchi et al. ..................... 106/35

FOREIGN PATENT DOCUMENTS 003431  4/1985  Japan .

Primary Examiner—Paul R. Michl
Assistant Examiner—John J. Guarriello
Attorney, Agent, or Firm—Oblon, Spivak, McClelland, Maier & Neustadt

[57] ABSTRACT

Curable resinous compositions which comprise (a) a metal element-containing inorganic filler which has been treated with an oxo acid of pentavalent phosphorus or a derivative thereof, which has the general formula:

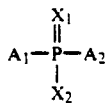

wherein $A_1$ is an organic group having at least one ethylenic double bond capable of radical polymerization and containing 5 to 60 carbon atoms, $A_2$ is a hydroxyl or mercapto group, a halogen atom or an organic group containing 1 to 60 carbon atoms, at least one of $A_1$ and $A_2$ contains at least one hydrocarbyl group containing 4 to 60 carbon atoms, $X_1$ is an oxygen or sulfur atom and $X_2$ is a hydroxyl or mercapto group of a halogen atom, and (b) at least one monomer capable of radical polymerization which is selected from the group consisting of methacrylates and acrylates, are useful for the production of cured articles which may be used in dentistry.

19 Claims, No Drawings

CURABLE RESINOUS COMPOSITION

BACKGROUND OF THE INVENTION

1. Field of the Invention

The present invention relates to curable resinous compositions, which contain an inorganic filler which has been surface-treated with an organophosphorus compound. The present curable resinous compositions may be used as materials for industrial use and as a biological hard tissue materials. As examples of such materials, there may be mentioned molding compositions, composite resins for dental use (filling and restoration materials, materials for making inlays, artificial crowns, artificial tooth, abutment construction materials), dental adhesives, denture base materials, impression materials, artificial bones and bone cements.

2. Discussion of the Background

The term "curable resinous composition" as used herein means a composition containing, as essential components, an inorganic filler and a polymerizable monomer.

Recently, in the field of dental care, compositions containing an inorganic filler and a polymerizable monomer, for example, composite resins for dental use, have come into use. The inorganic fillers used in composite resins for dental use are generally subjected to preliminary surface treatment. The surface treatment improves the wettability at the filler-polymerizable monomer interface, makes it possible to increase the filler content, and improves the dispersibility of the filler in the composition. As a result, composite resin moldings obtained by polymerization of the monomer have improved mechanical strength owing to good adhesion at the filler-resin interface. Known in the art as surface treating agents for such purposes are silane coupling agents, typically γ-methacryloyloxypropyltrimethoxysilane.

More broadly, in the industrial field, there are known, as other surface treating agents for inorganic fillers, titanate coupling agents, zircoaluminate type coupling agents, higher alkyl alcohols, higher fatty acids, organophosphate esters, and so forth. Among them, the organophosphate esters are related to the present invention and therefore are summarized below.

Japanese Patent Publication No. 60-3431 discloses inorganic fillers surface-treated with organophosphate esters of the formula:

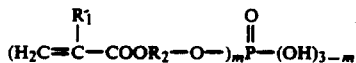

wherein $R_1$ is a hydrogen atom or a methyl group and $R_2$ is an alkylene group containing 2 to 6 carbon atoms or a halogen-substituted derivative thereof, a polyoxyethylene group of the following formula:

$$-CH_2-CH_2-(O-CH_2-CH_2)_n- \quad (n=1 \text{ to } 20)$$

or a polyoxypropylene group of the following formula:

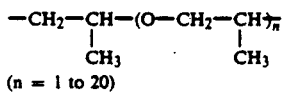

(n = 1 to 20)

Japanese Laid-open Patent Application Kokai No. 59-170131 discloses inorganic powders surface-treated with one or more organophosphorus compounds of the general formula:

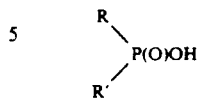

wherein R and R' are the same or different and each is an alkyl, alkenyl, aryl, alkoxy, alkenoxy or aryloxy group containing 1 to 30 carbon atoms or a group derived from these organic groups by substitution.

In addition, Japanese Laid-open Patent Applications Kokai Nos. 56-54795, 57-128728, 57-168954, and 57-198735, describe similar technical ideas.

These known resinous compositions for industrial use comprise a polymer and a surface-treated inorganic filler. Since the polymer has no or few reactive groups, the possibility that the polymer may be bound chemically to the surface-treating agent to a high degree is small and therefore only limited improvements in mechanical properties are attained. Accordingly, resinous compositions in which the resin is bound to the surface-treating agent to a high degree and which can give good mechanical properties are highly desirable.

Furthermore, compositions for dental use, to which an aspect of the present invention is directed, are required to possess water resistance, which is a very important property since the cured moldings from said compositions may be used in the oral cavity for a prolonged period of time. Accordingly, resinous compositions of good water resistance are also desired.

The above-cited prior art references are not concerned with improving the water resistance of the respective resinous compositions or of the applicability of the compositions in dentistry. Thus, it is impossible to anticipate from said references that the known organophosphorus compounds might be effective in achieving the objects of the present invention.

Inorganic fillers in conventional resinous compositions, especially those in dental use, mostly have a high silicon content (for example, silica and silica-based glasses). Only in very rare cases, have inorganic fillers containing a metal or a metal oxide or salt as a main constituent, been put to practical use in resinous compositions.

As the main reason why such metal element-containing inorganic fillers have not been used in resinous compositions, there may be mentioned the fact that the technology of surface treatment of said fillers has not been established. The surface treatment effect of known silane- or titanium-containing surface-treating agents, on these inorganic fillers, is not so remarkable as those on silica. Therefore, resinous compositions containing large amounts of these fillers treated with known surface treating agents suffer from disadvantages such as decreased strength (in particular under wet conditions) or dislodgement of the filler due to insufficient bonding at the resin-inorganic filler interface.

However, it might be expected that the use of a metal, metal oxide or metal salt as an inorganic filler might give resinous compositions possessing more favorable characteristics as compared with the conventional silica-containing compositions.

For instance, replacement of silica with a metal oxide such as alumina or zirconia might give composite resins for dental use which have an aesthetic appearance, good mechanical strength, and good chemical stability, and incorporation of a filler close in composition to a natural tooth, such as hydroxyapatite, might provide dental adhesives having good biocompatibility. The use of a metal filler could make it possible to develop new types of composites for dental use which have ductility and toughness.

In view of the foregoing, the possibility of a surface treatment technology effectively applicable to the above-mentioned metal element-containing inorganic fillers has been investigated.

SUMMARY OF THE INVENTION

Accordingly, it is an object of the present invention to provide resinous compositions which contain a surface-treated, metal element-containing inorganic filler and a monomer capable of radical polymerization, which yield cured articles which possess good mechanical properties.

It is another object of the present invention to provide resinous compositions which yield cured articles which are water resistant.

It is another object of the present invention to provide resinous compositions which exhibit good bonding at the resin-inorganic filler interface.

It is another object of the present invention to provide resinous compositions which contain a filler which is a metal, metal oxide, or metal salt.

It is another object of the present invention to provide resinous compositions which contain a filler which is a metal, metal oxide, or metal salt and yield cured articles which possess good mechanical strength.

It is another object of the present invention to provide resinous compositions which contain a filler which is a metal, metal oxide, or metal salt and yield cured articles in which the filler is not dislodged.

It is another object of the present invention to provide resinous compositions which are biocompatible.

These and other objects which will become apparent during the course of the following detailed description have been achieved by the present inventors' discovery that organophosphorus compounds having a specific molecular structure can serve as very effective surface-treating agents for metal element-containing inorganic fillers.

Thus, the resinous composition provided by the present invention is a curable resinous composition which comprises:

(a) a metal element-containing inorganic filler preliminarily treated with an oxo acid of pentavalent phosphorus or a derivative thereof, which has the general formula:

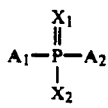

(I)

wherein $A_1$ is an organic group having at least one ethylenic double bond capable of radical polymerization and containing 5 to 60 carbon atoms, $A_2$ is a hydroxyl or mercapto group, a halogen atom or an organic group containing 1 to 60 carbon atoms, at least one of $A_1$ and $A_2$ contains at least one hydrocarbyl group containing 4 to 60 carbon atoms, $X_1$ is an oxygen or sulfur atom and $X_2$ is a hydroxyl or mercapto group or a halogen atom, and (b) at least one monomer capable of radical polymerization which is selected from the group consisting of methacrylates and acrylates.

DETAILED DESCRIPTION OF THE PREFERRED EMBODIMENTS

The resinous compositions according to the present invention are preferably used as compositions for dental use and, in the following, the invention is described with particular reference with compositions for dental use. It is to be noted, however, that the range of applicability of the resinous compositions according to the invention is not limited to the field of dentistry.

The inorganic filler to be used in the resinous composition of the present invention is characterized in that it contains a metal element as a component thereof. Metal elements include the elements positioned to the left of the line connecting boron and astatine in the long form of the periodic table, with the exclusion of hydrogen and the elements positioned on the line, namely B, Si, As, Te, and At. Among such elements, Al, Mg, Ca, Ti, Cr, Fe, Co, Ni, Cu, Zn, Sr, Zr, Pd, Hg, Sn, Ba, Pt, Au, and La, for example, are particularly useful in achieving the objects of the present invention.

The metal element can take various forms in the inorganic filler. For example, it may be contained in the filler in the form of an oxide such as $Al_2O_3$, ZnO, CaO, $TiO_2$, $ZrO_2$, $La_2O_3$, BaO, $Fe_2O_3$ or $SrO_2$; a hydroxide, such as $Al(OH)_3$; a halide, such as $CaF_2$; a sulfate, such as $BaSO_4$ or $CaSO_4$; a carbonate, such as $CaCO_3$; a phosphate, such as $CaHPO_4$, $Ca(H_2PO_4)_2$, $Ca_3(PO_4)_2$, $Ca_2P_2O_7$, $Ca(PO_3)_2$, $Ca_4P_2O_9$, $Mg_2P_4O_{12}$, $Al(PO_3)_2$ or $AlPO_4$; or the like.

Such metal compounds may occur, in the inorganic filler, either as a single component or as a constituent of a multicomponent system, such as a ceramic or a mineral. In a multicomponent system, the system can of course contain a plurality of metal elements and may further contain components other than metal elements, for example $SiO_2$, $P_2O_5$, $B_2O_3$, $Si_3N_4$, SiC, $B_4C$ and BN. As examples of such systems, there may be mentioned $K_2O.TiO_2$, $BaO.TiO_2$, $CaO.Al_2O_3$, zircon (the $SiO_2$—$ZrO_2$ system), sialon (the $SiO_2$—$Al_2O_3$—$Si_3N_4$ L system), La-glass ceramics (the $La_2O_3$—$Al_2O_3$—$SiO_2$ system; e.g., Shott GM 31-684®), Ba-glasses (the BaO—$Al_2O_3$—$B_2O_3$—$SiO_2$ system; e.g. Shott GM 27-884®, Shott 8235®, Ray-Sorb T-2000®, Ray-Sorb T-3000®), Sr-glasses (the $SrO_2$—$Al_2O_3$—$SiO_2$ system, e.g. Shott GM 32-087®, Ray-Sorb T-4000®) and, further, the so-called bioglasses, for example various CaO—$P_2O_5$-containing glass ceramics and hydroxyapatite. Furthermore, in addition to such forms as mentioned above, metal powders as such may also be used as fillers and, in this case, metals are used as simple substances or in the form of alloys.

In any of the fillers mentioned above, it is essential that the inorganic filler should be substantially insoluble in water, since the resinous composition includes dental applications in which it is used under highly wet conditions. The term "substantially insoluble in water" as used herein means that the inorganic filler has a saturated concentration of 0.1% by weight or less in water at room temperature.

The inorganic filler may have any form or shape without any limitation. Various sizes and forms, such as spherical, crushed, needle-like, whisker and platelet forms, may be used depending on the intended use of the composition. The particle size of the inorganic filler is not critical but, generally, a size within the range of 5 nm to 0.5 mm is preferred. The "particle size" as so called herein is expressed in terms of the mean of the maximum diameter and the minimum diameter of the filler.

The most characteristic feature of the invention lies in that the above filler is used after preliminary surface treatment with an oxo acid of pentavalent phosphorus or a derivative thereof, which is represented by the general formula (1) and sometimes hereinafter referred to as "organophosphorus compound" as well. Hereinafter, the inorganic filler in the untreated state is sometimes referred to as "inorganic filler (A)".

As particular examples of the "ethylenic double bond capable of radical polymerization", which constitutes a structural characteristic of the above-mentioned organophosphorus compound (1), there may be mentioned the following:

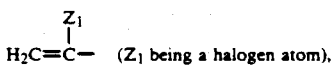

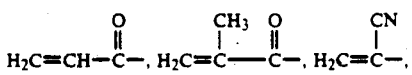

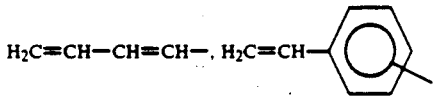

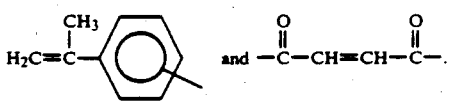

Among such ethylenic double bonds, the ethylenic double bonds of acrylic acid, methacrylic acid, or styrene are particularly preferred. When inorganic filler (A) is treated with an organophosphorus compound which is the same as the organophosphorus compound (1) except for the absence of the above-mentioned double bond, the adhesion between filler and resin matrix is very poor, and accordingly, the objects of the invention can never be accomplished.

The term "organic group" as used herein includes:
(a) hydrocarbyl groups which may optionally have one or more substituents selected from the group consisting of halogen, hydroxyl, carboxyl, mercapto, cyano, phosphono, and —O—P(O)(OH)$_2$ groups,
(b) groups resulting from coupling of at least one of the above-mentioned hydrocarbyl groups to at least one of the following linking groups:

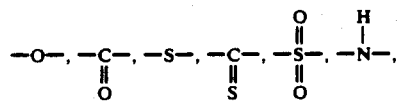

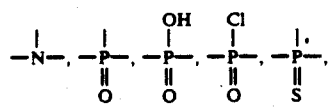

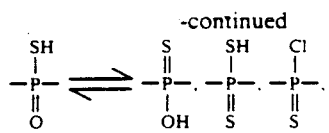

and complex linking groups resulting from coupling of at least two of the above linking groups.

The following typical examples will serve for more detailed illustration.

Examples of the hydrocarbyl groups (a) include:

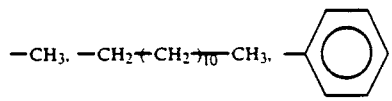

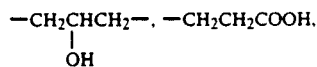

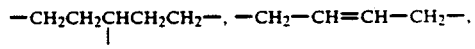

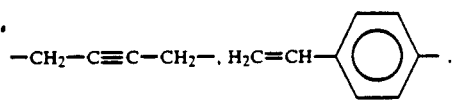

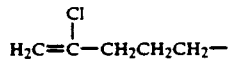

Examples of the groups (b) derived from at least one hydrocarbyl group (a) and at least one linking group include:

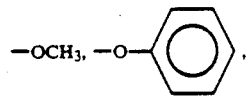

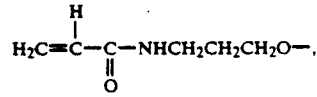

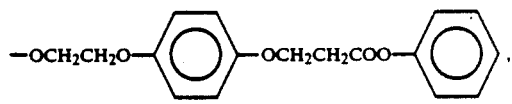

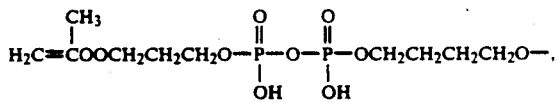

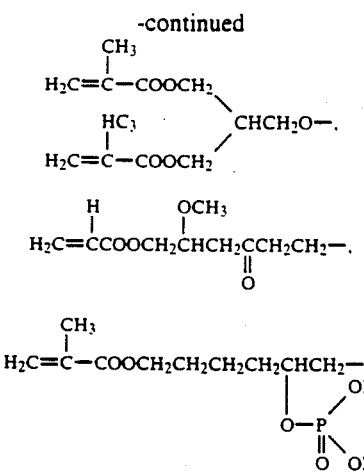

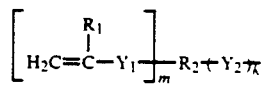

The hydrocarbyl groups having 4 to 60 carbon atoms, which may be contained in at least one of the organic groups $A_1$ and $A_2$ of said formula (1) are the same groups as mentioned above. Structures resulting from substitution of the hydrocarbyl group with three or more hyrophilic substituents, such as hydroxyl, carboxyl, phosphono, and —O—P(O)(OH)$_2$ groups, however, are disadvantageous in achieving the objects of the present invention since such hydrophilic substituents decrease the hydrophobicity of the hydrocarbyl group.

When the hydrocarbyl group contains less than 4 carbon atoms, the resulting resinous composition may often be unsatisfactory in water resistance. When the number of carbon atoms in question is at least 4, preferably at least 5, the water resistance attained is at a level satisfactory for dental applications. In particular, when the number of carbon atoms is at least 8, good water resistance is obtained.

The number of carbon atoms in $A_1$ has an influence on the effects of surface treatment. When the number of carbon atoms is within the range of 5 to 60, the effects of surface treatment are such that desirable physical properties required for dental use can be attained. When $A_2$ is an organic group, the number of carbon atoms in $A_2$ also has an influence on the effects of surface treatment and should preferably be not more than 60.

Among the organophosphorus compounds of general formula (1), those compounds mentioned below are particularly preferred in view of reactivity with inorganic fillers, copolymerizability with polymerizable monomers (b), and ease of synthesis.

(i) Compounds of general formula (1) wherein $A_1$ is a univalent organic group of the general formula:

$$\left[ H_2C=\underset{\underset{R_1}{|}}{C}-Y_1 \right]_m R_2 (Y_2)_k$$

in which $R_1$ is a hydrogen atom or a methyl group, $R_2$ is an organic group which contains a total of 4 to 40 carbon atoms, contains at least one hydrocarbyl group having 4 to 40 carbon atoms, has a valence of $(m+1)$ and is bound to each of the $Y_1$ and $Y_2$ groups with a carbon atom contained therein, $Y_1$ is —COO—, —COS— or —CONR$_3$— ($R_3$ being a hydrogen atom or a hydrocarbyl group containing 1 to 6 carbon atoms), $Y_2$ is an oxygen or sulfur atom or

($R_3$ being defined as above), m is an integer of 1 to 4 and k is an integer of 0 or 1, and wherein $A_2$ is a hydroxyl or mercapto group or a halogen atom.

Preferred among the compounds (i) mentioned above compounds in which $X_1$ is an oxygen atom and $X_2$ and $A_2$ each is a hydroxyl group. The group of these compounds is hereinafter referred to as "group (i)-a".

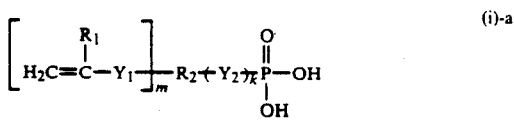

The organophosphorus compounds (i)-a are most effective in treating base metal element-containing inorganic fillers. As examples of the base metal element, there may be mentioned Al, Mg, Ca, Ti, Fe, Co, Cr, Ni, Cu, Zn, Sr, Zr, Sn, Ba, La, and Cr. The (i)-a compounds are particularly effective in treating metal oxides such as $Al_2O_3$, $TiO_2$, $ZrO_2$, $Fe_2O_3$, and ZnO; metal salts such as $CaCO_3$, $Ca_3(PO_4)_2$ and $AlPO_4$; hydroxyapatite; and metal powders containing Ti, Fe, Co, Cr, Ni, Cu, Zn, and Sn. Specific examples of the group (i)-a compounds include:

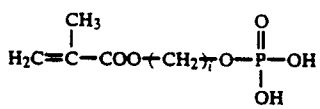

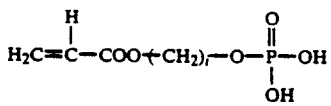

(i being an integer of 4 to 40)

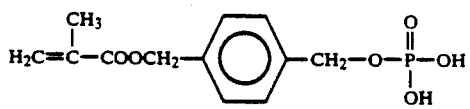

-continued
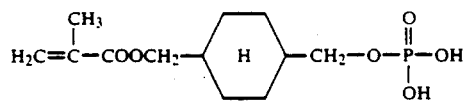
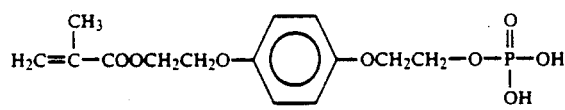
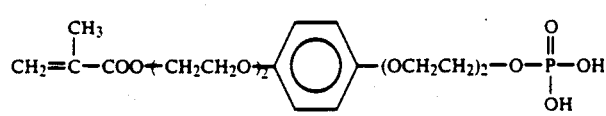
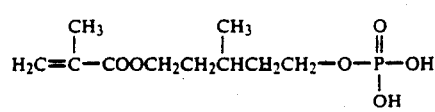
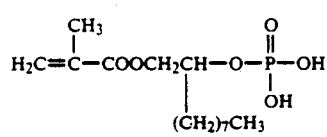
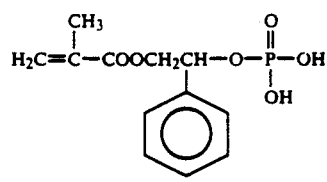
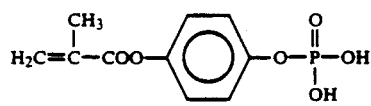
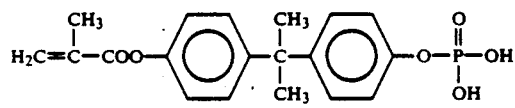
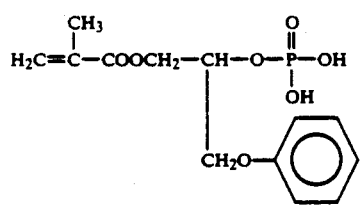
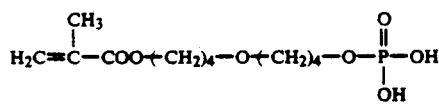
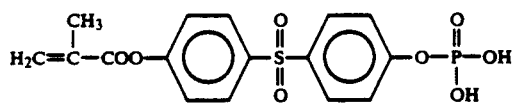
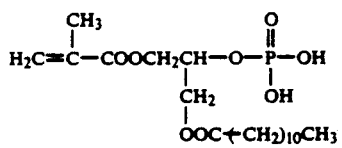

-continued
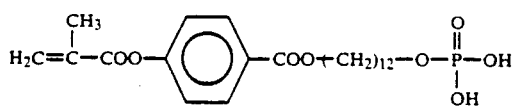
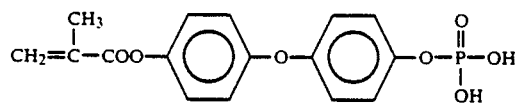
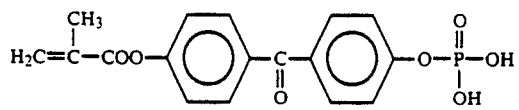
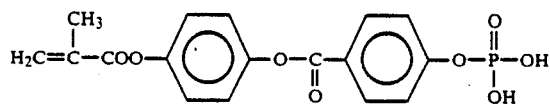
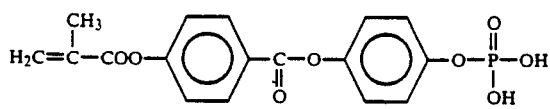
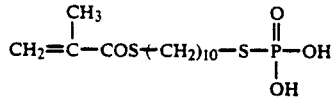
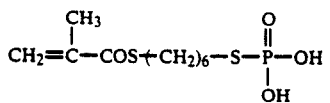
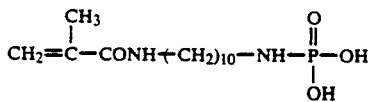
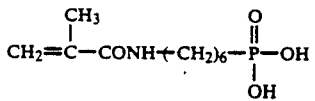
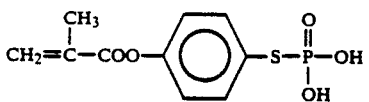
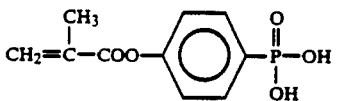
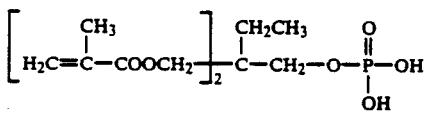
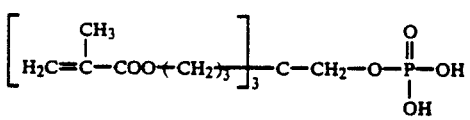
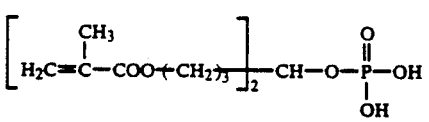

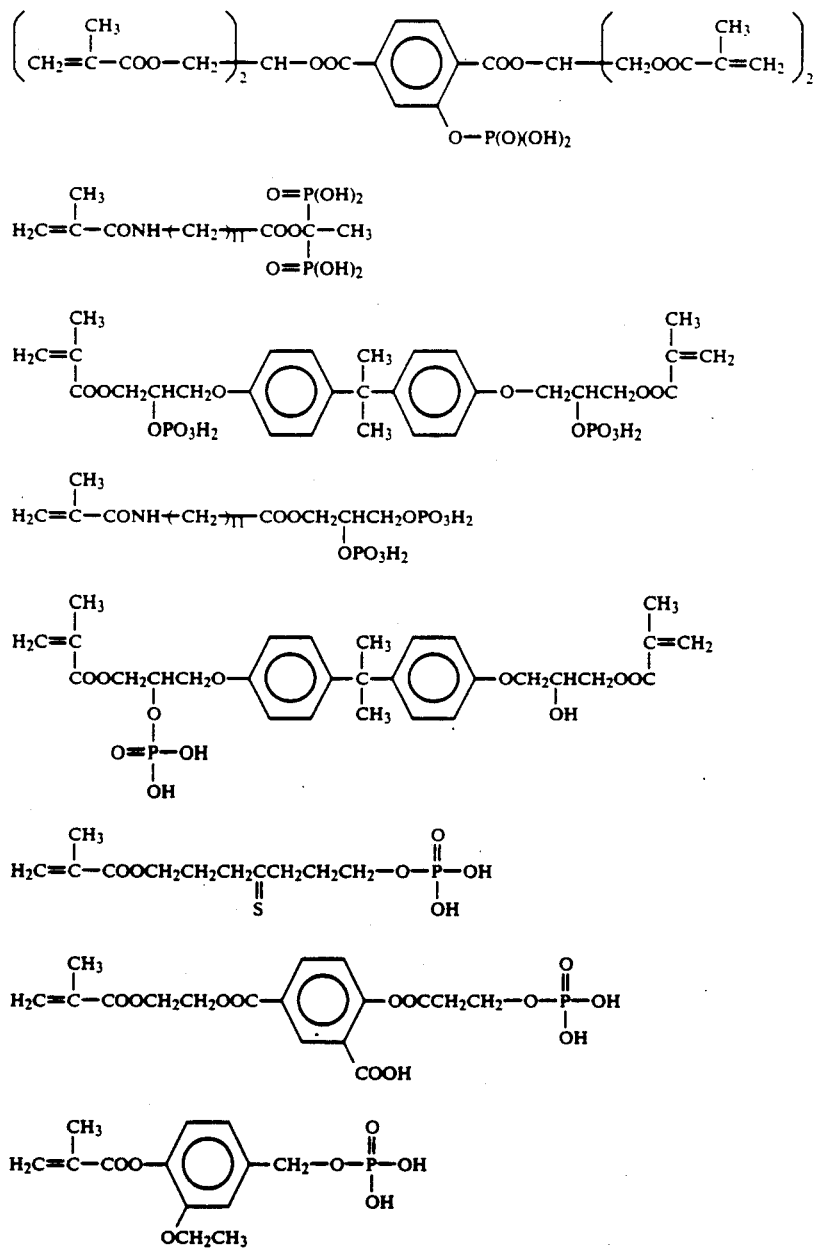

Another preferred group of compounds, group (i)-b, includes those compounds (i) mentioned above in which, in general formula (1), $X_1$ is an oxygen atom and $A_2$ and $X_2$ are each a halogen atom, such as chlorine, bromine, fluorine, or iodine. When the halogen is chlorine, these compounds may be represented by the general formula:

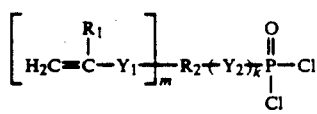

Typical examples of such compounds are as follows:

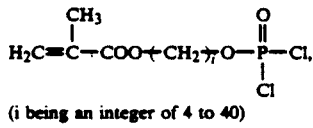

(i being an integer of 4 to 40)

-continued
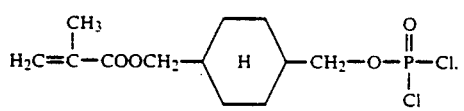
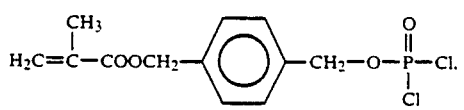
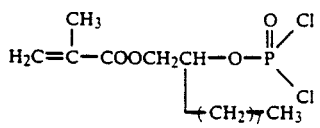
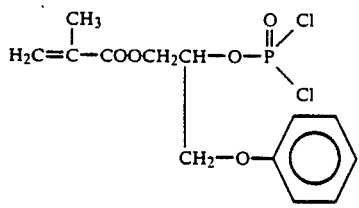
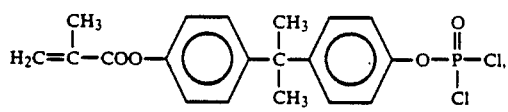
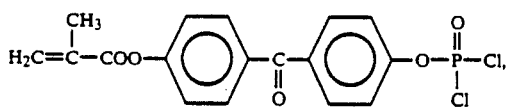
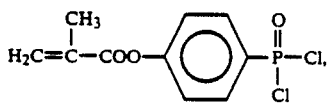
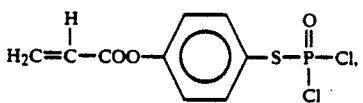
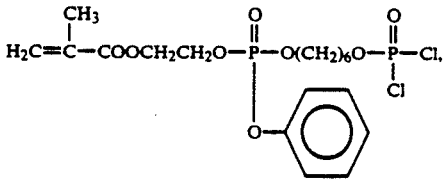
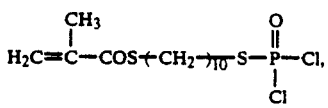
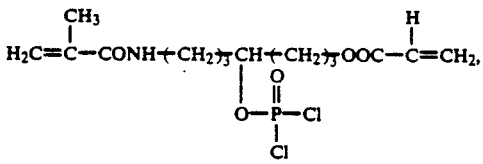

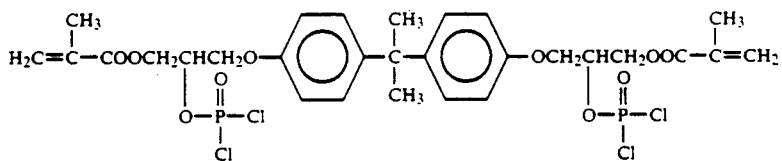

A third group of preferred compounds, group (i)-c, includes those compounds (i) mentioned above in which, in general formula (1), $X_1$ is a sulfur atom and $A_2$ and $X_2$ each is a hydroxyl or mercapto group or a halogen atom.

 (i)-c

The group (i)-c organophosphorus compounds produce good effects in the surface treatment of not only base metal element-containing inorganic fillers but also noble metal element-containing inorganic fillers. As examples of the noble metals, there may be mentioned Pd, Ag, Pt, and Au. Examples of the —P(S)A₂X₂ group include

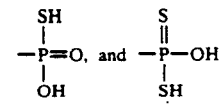

Among the above examples,

has the tautomeric form

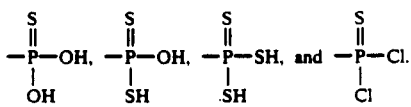

can occur in the tautomeric form $$-\overset{SH}{\underset{SH}{P}}=O.$$

Specific examples of the (i)-c group compounds are as follows:

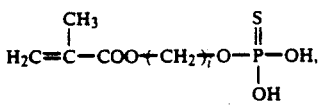

(i being an integer of 4 to 40)

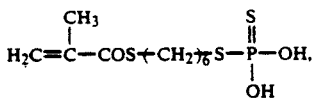

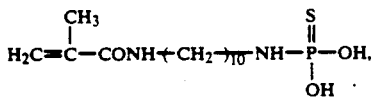

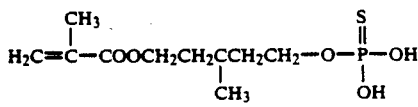

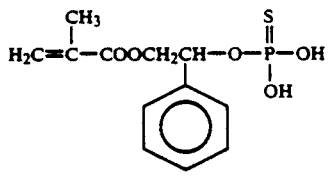

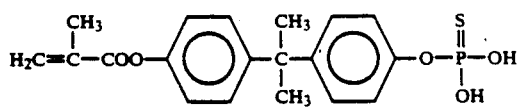

-continued
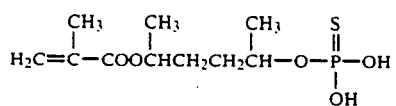
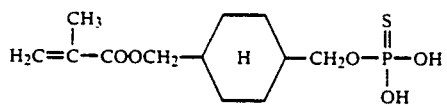
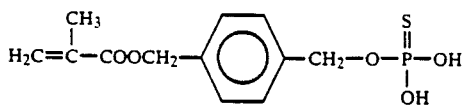
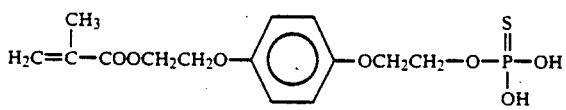
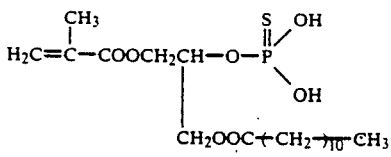
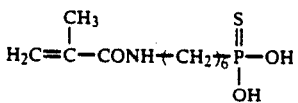
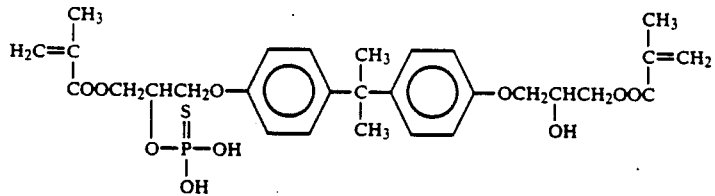
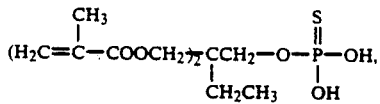
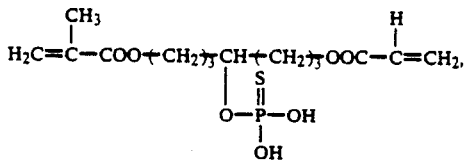
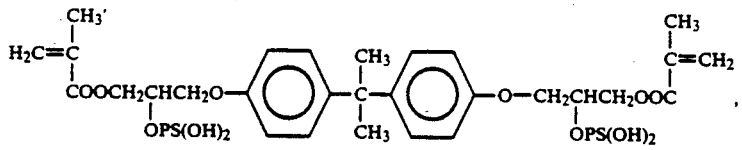
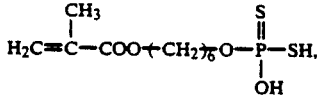
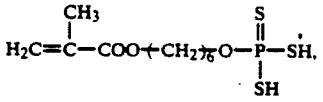

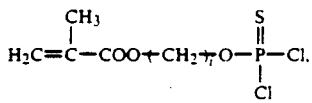

(i being an integer of 4 to 40)

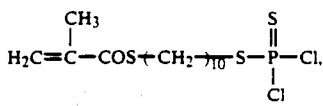

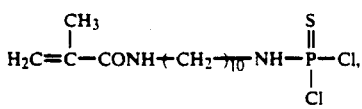

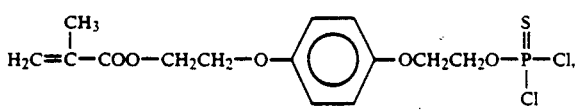

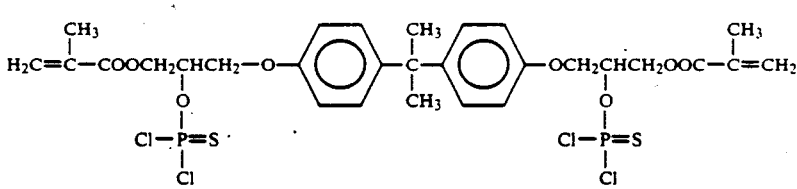

Also of value in the practice of the invention are the following compounds:

(ii) Compounds of general formula (1) wherein $A_1$ is a univalent organic group of the general formula:

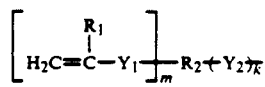

in which $R_1$, $R_2$, $Y_1$, $Y_2$, m and k are as defined hereinabove in relation to the compounds (i) and wherein $A_2$ is a univalent organic group of the general formula:

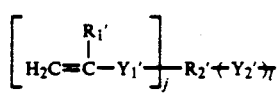

in which $R_1'$ is a hydrogen atom or a methyl group, $R_2'$ is an organic group which contains 1 to 40 carbon atoms, has a valence of (j+1) and is bound to each of the $Y_1'$ and $Y_2'$ groups with a carbon atom contained therein, $Y_1'$ is —COO—, —COS—, or —CONR$_3'$— ($R_3$ being a hydrogen atom or a hydrocarbyl group containing 1 to 6 carbon atoms), $Y_2'$ is an oxygen or sulfur atom or

($R_3$ being defined as above), j is an integer of 0 to 4 and l is an integer of 0 or 1.

Among the compounds (ii) mentioned above, those in which, in general formula (1), $X_1$ is an oxygen atom and $X_2$ is a hydroxyl group constitute a preferred group, hereinafter referred to as group (ii)-a.

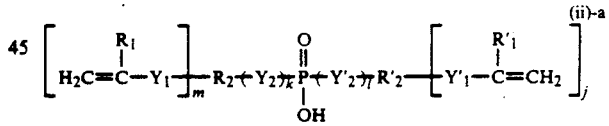

The organophosphorus compounds of group (ii)-a are also effective in treating base metal element-containing inorganic fillers as mentioned above in regard to organophosphorus compounds (i)-a.

Typical examples of the compounds (ii)-a are as follows:

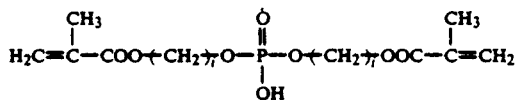

(i being an integer of 4 to 40)

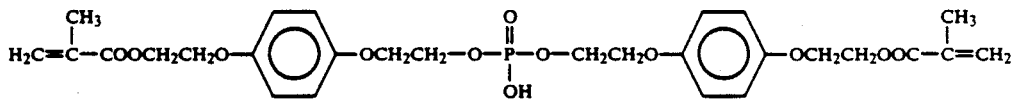

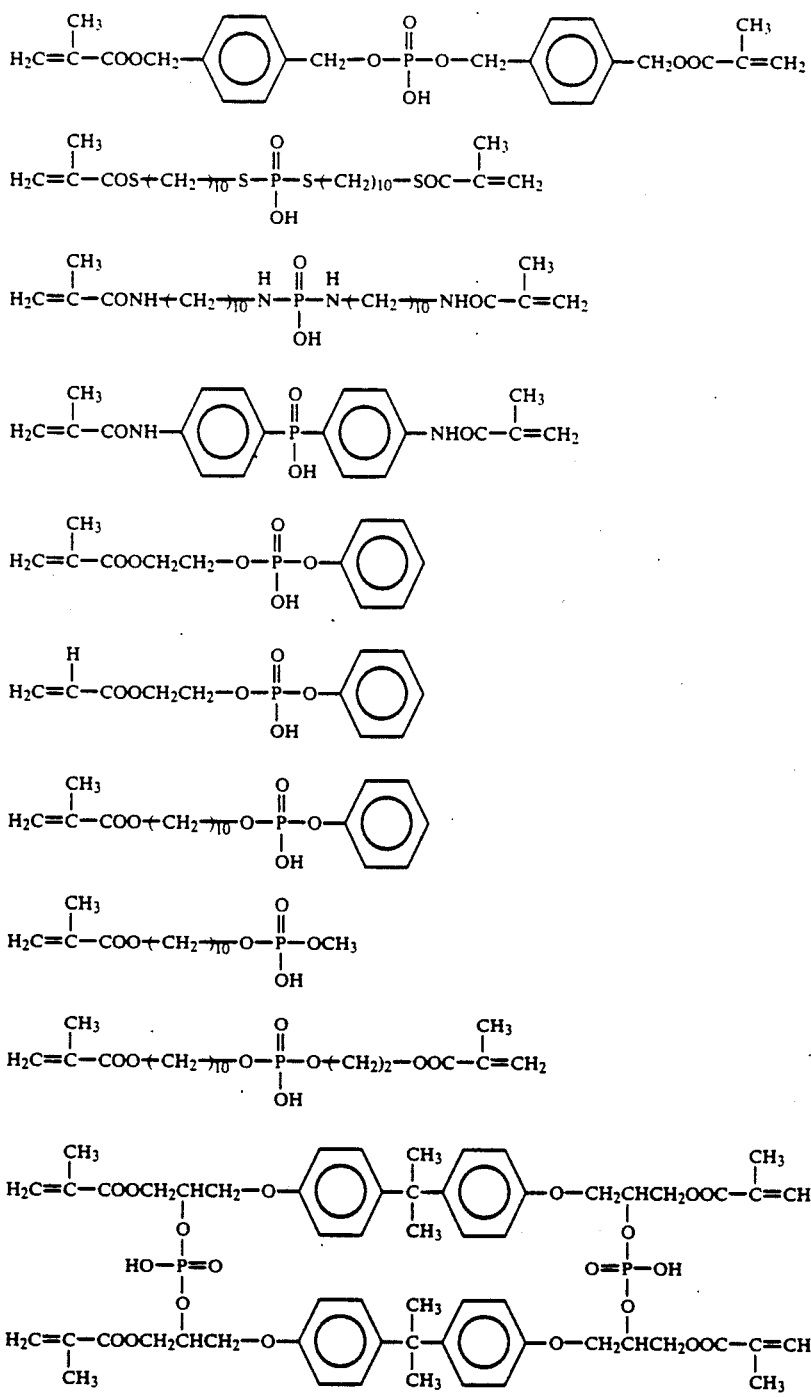

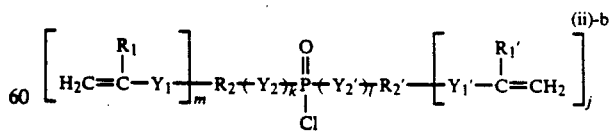

Another group (hereinafter referred to as group (ii)-b) of preferred compounds among the compounds (ii) includes those compounds (ii) in which $X_1$ is an oxygen atom and $X_2$ is a halogen atom, such as chlorine, bromine, fluorine, or iodine.

When the halogen atom is chlorine, the (ii)-b compounds may be represented by the structural formula:

The organophosphorus compounds (ii)-b, which correspond to derivatives of the compounds (ii)-a wherein a hydroxyl group of $X_2$ is substituted for chlorine atom, are comparable in surface treatment effects to the compounds (ii)-a. The same relationship exists between the groups (i)-b and (i)-a.

Typical examples of the compounds (ii)-b are as follows:

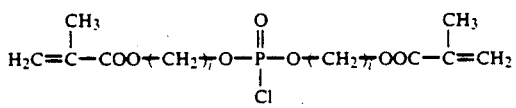
(i being an integer of 4 to 40)

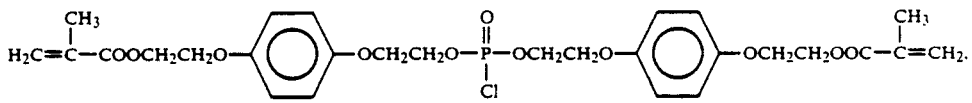

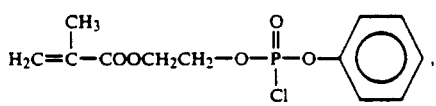

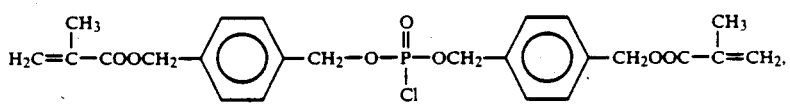

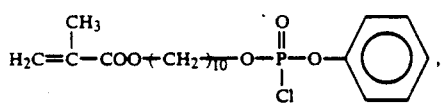

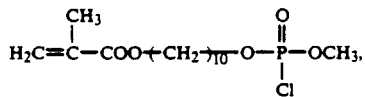

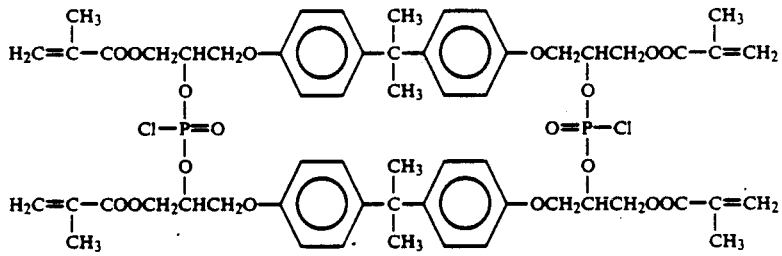

Among the compounds (ii), those in which $X_1$ is S and $X_2$ is a hydroxyl or mercapto group or a halogen atom are hereinafter referred to as compounds (ii)-c, and are represented by the formula:

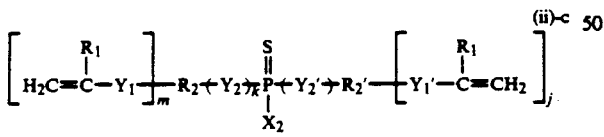 (ii)-c

Like the organophosphorus compounds (i)-c, the compounds (ii)-c are effective in treating base metal or noble metal-containing inorganic fillers. The compounds (ii)-c can be synthesized more readily and have higher stability than the compounds (i)-c and therefore can be utilized more advantageously.

Typical examples of the

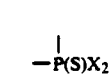

group in compounds (ii)-c are as follows:

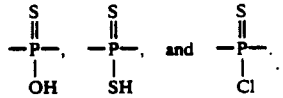

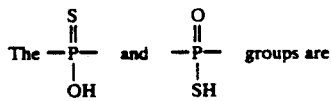 groups are tautomers to each other.

Typical examples of the compounds (ii)-c are as follows:

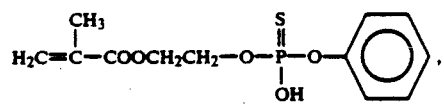

-continued
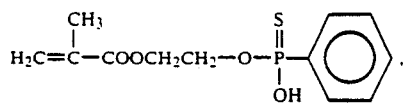
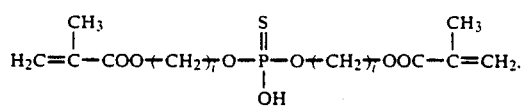
(i being an integer of 4 to 40)
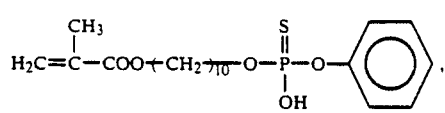
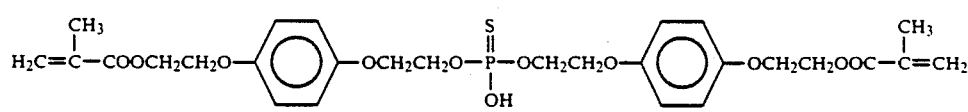
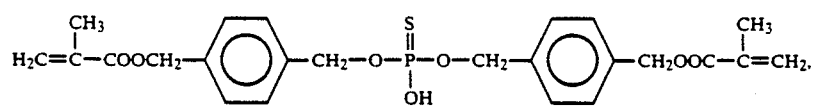
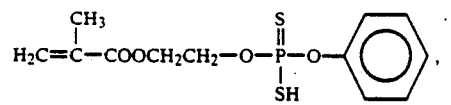
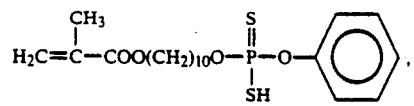
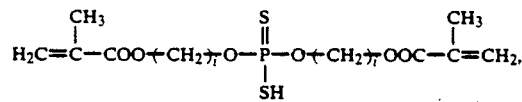
(i being an integer of 4 to 40)
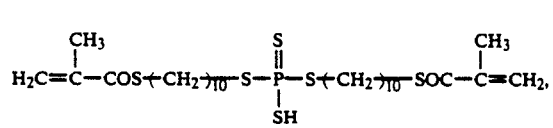
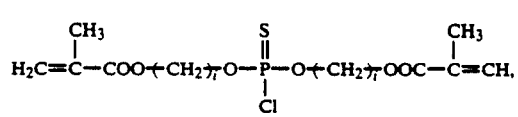
(i being an integer of 4 to 40)
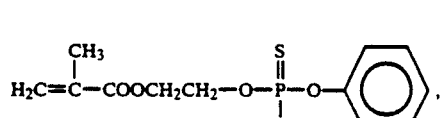
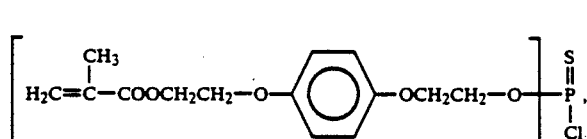

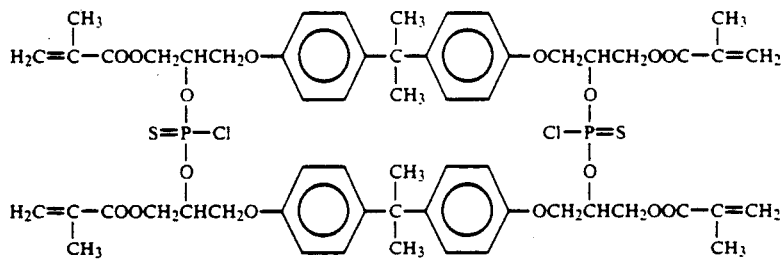

Furthermore, in accordance with the present invention, the following, group (ii), organophosphorus compounds can be used as well. Group (iii) compounds have the general formula (1), wherein $A_1$ is a univalent organic group of the general formula:

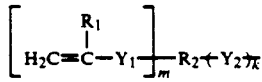

in which $R_1$, $R_2$, $Y_1$, $Y_2$, m, and k are defined as above for the compounds (ii) and wherein $A_2$ is a univalent organic group of the general formula:

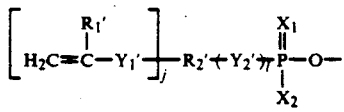

wherein $R_1'$, $R_2'$, $Y_1'$, $Y_2'$, j, and l are defined as above for the compounds (ii) and $X_1$ and $X_2$ are defined as above for the compounds (i).

Such compounds have the structural formula:

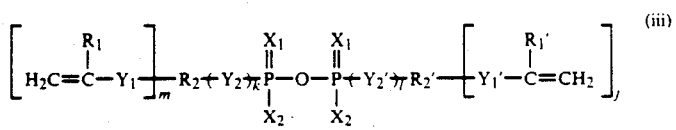

When neither $X_1$ nor $X_2$ contains a sulfur atom, the organophosphorus compounds (iii) are as effective in treating base element-containing fillers as the sulfur-free compounds among those mentioned above. On the other hand, those compounds (iii) in which $X_1$ and/or $X_2$ contains a sulfur atom are remarkably effective also in treating noble metal element-containing fillers, like the sulfur-containing compounds among the compounds mentioned above. In either case, those compounds (iii) in which $R_1=R_1'$, $R_2=R_2'$, $Y_1=Y_1'$, $Y_2=Y_2'$, m=j and k=l, namely which are symmetrical, are preferred for the reason that they can be synthesized with ease.

Typical examples of the compounds (iii) are as follows:

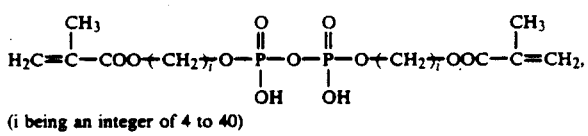

(i being an integer of 4 to 40)

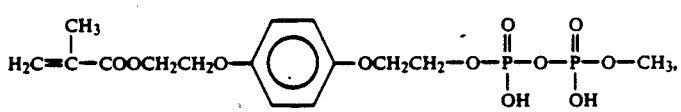

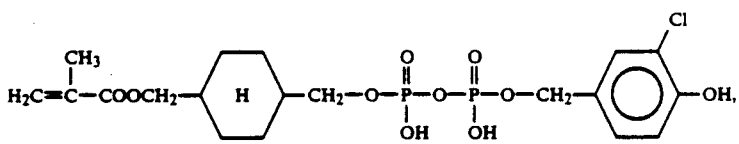

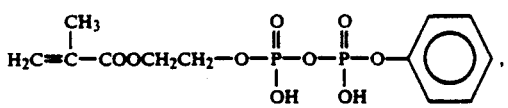

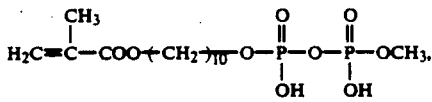

-continued
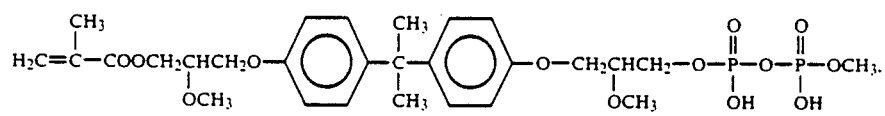
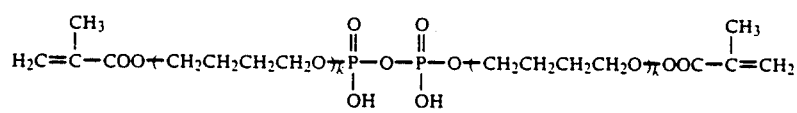
(k being an integer of 1 to 14)
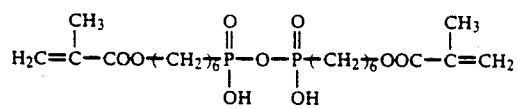
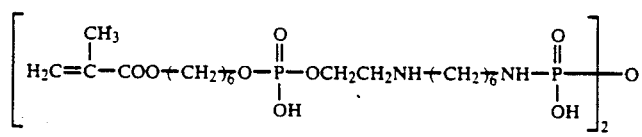
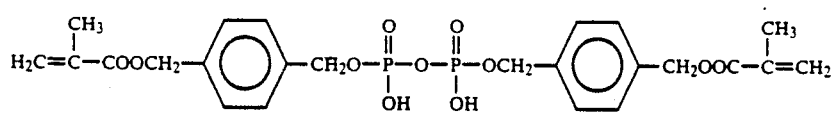
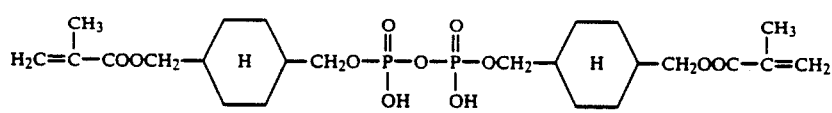
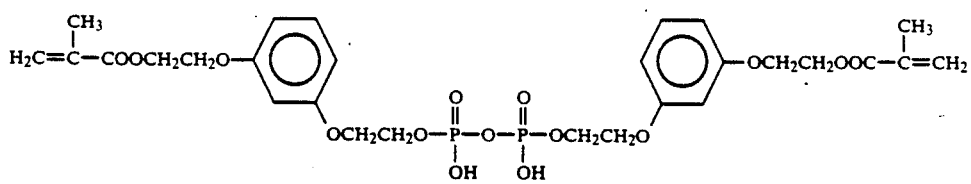
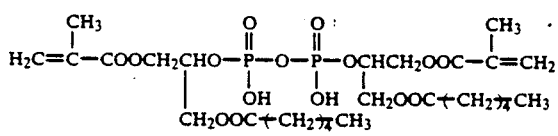
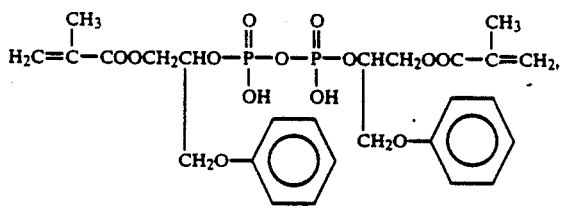
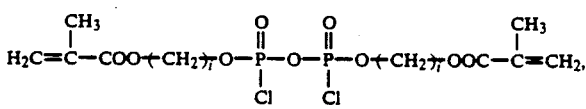
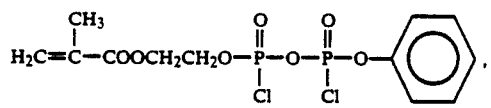
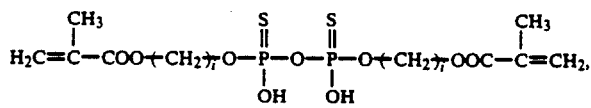

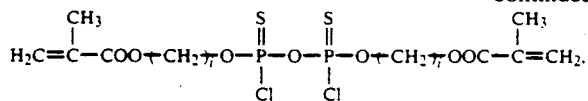

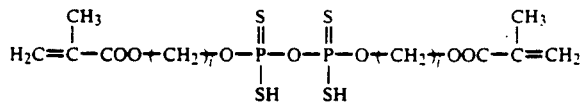

(i being an integer of 4 to 20)

In any of the organophosphorus compounds (i) through (iii), the group $R_2$ should preferably possess a long chain length but have no long, bulky, branched side chains. The reason is presumably that when compounds having such $R_2$ group are used, the inorganic filler surface can be covered to a satisfactory extent with surface treating agent molecules.

When m is equal to 1, the following is a particularly preferred structure of $R_2$:

wherein h is 0 or 1, and when h=0, $R_4$ is a hydrocarbyl group containing 4 to 20 carbon atoms and $Y_3$ is an oxygen atom, and when h=1, $R_4$ is a hydrocarbyl group containing 2 to 9 carbon atoms, $R_5$ is a hydrocarbyl group containing 4 to 20 carbon atoms, and $Y_3$ is an oxygen atom, —COO— or —OOC—.

Typical examples of $R_2$ are as follows:

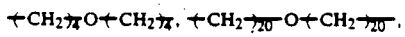

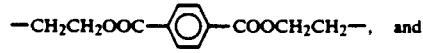

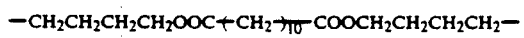

Another preferred structure of $R_2$ is the following:

wherein i is an integer of 4 to 40.

In the practice of the present invention, other organophosphorus compounds, such as shown below, may also be used suitably as surface treating agents in addition to the above-mentioned organophosphorus compounds (i) to (iii).

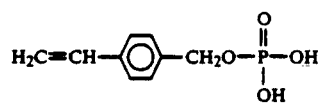

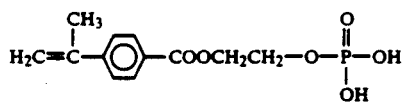

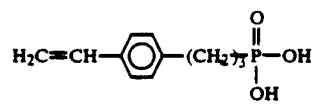

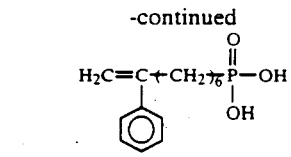

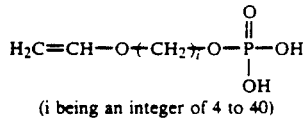

(i being an integer of 4 to 40)

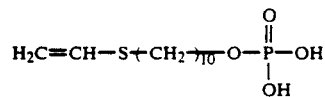

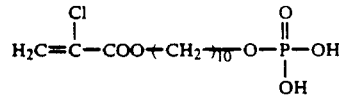

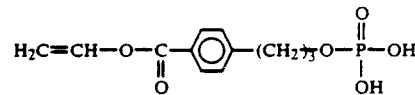

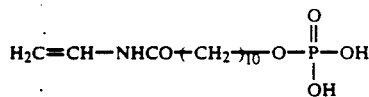

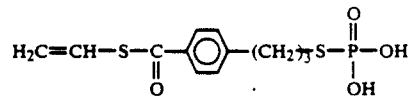

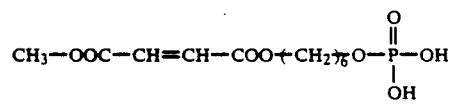

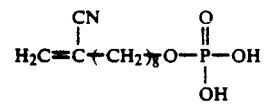

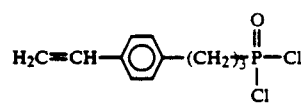

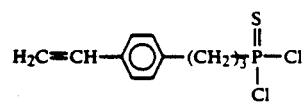

-continued

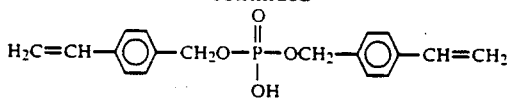

In synthesizing the above-described organophosphorus compounds, the following, for instance, may serve as references: G. M. Kosolapoff, *Organophosphorus Compounds*, Wiley (1950); Ye. L. L. Gefter, *Organophosphorus Monomers and Polymers*, Pergamon Press (1962); The Society of Synthetic Organic Chemistry, Japan (ed.), *Modern Organic Synthesis Series 5, Organophosphorus Compounds*, Gihodo (1971); and *Bielsteins Handbuch der Organischen Chemie*, Springer-Verlag.

More specifically, the methods of synthesis disclosed in Japanese Laid-open Patent Applications Kokai Nos. 58-128393, 58-192891, 58-21687, 58-21688, 59-139392, 59-135272, 59-142268, 60-166363, 60-166364, and 57-151607 may also be applicable.

The surface modification of inorganic fillers (A) with organophosphorus compound (1) can be carried out by any of the methods generally known for surface treatment of powder materials with surface treating agents and, in brief, by the wet method or dry method.

The wet method involves suspending an inorganic filler (A) and an organophosphorus compound (1) in an appropriate amount of a solvent such as water, alcohol, hexane, benzene, toluene, xylene, or the like and stirring the resulting slurry to a sufficient extent. In this case, the optimum conditions, namely the optimum solvent, reaction temperature, and reaction time, may vary depending on the combination of inorganic filler (A) and organophosphorus compound (1) but can be easily determined by one skilled in the art. After a sufficient period of stirring, the solvent is removed by evaporation under a reduced pressure, filtration, lyophilization, or the like method, whereby the surface treatment is completed.

In this case, it is desirable that any of the above-mentioned treatment steps mentioned above involve a heating step. The heating may be effected during stirring the slurry composed of inorganic filler (A), organo-phosphorus compound (1), and solvent; during evaporation of the solvent; or after the evaporation. In particular, heating the slurry will increase the dispersibility of the filler and thus allow it to be surface-treated evenly. The heating temperature is preferably within the range of 50° C. to 150° C. At temperatures below 50° C., the effect of heating will be poor, while heating at temperatures exceeding 150° C. may cause the double bond capable of radical polymerization to react.

Those organophosphorus compounds (1) in which $X_2$ is a hydroxyl or mercapto group may also be used in the form of an alkali metal or ammonium salt thereof so that they can be reacted with the inorganic filler in a desalting reaction.

The dry method involves charging the inorganic filler (A) into a mixer, such as a Henschel fluidizing mixer or a ribbon blender, and adding, while stirring, the organophosphorus compound (1) directly or in the form of a solution by spraying. In this case, the stirring is desirably carried out with heating. This method is suited for the treatment of large-quantities of the filler.

The organophosphorus compound is used preferably in an amount sufficient to coat most of the inorganic filler surface with a monomolecular layer thereof. The required amount can be estimated on the basis of the specific surface area of inorganic filler, as measured by the BET method, and the proportion of metal element on the surface of the filler. The required quantity of organophosphorus compound increases with decreasing inorganic filler diameter and increasing metal element content on the surface. Generally speaking, in consideration of above factors, the organosphosphorus compound (1) is used in an amount of 0.01 to 100 parts by weight per 100 parts by weight of inorganic filler. Of course, the optimal quantity of organophosphorus compound (1) should be determined based on the results of preliminary experiments so that the physical characteristics of the resinous composition for a specific use can be maximized.

The quantity of organophosphorus compound (1) on inorganic filler (A) can be estimated by elemental analysis, infrared spectroscopy, or fluorescent X-ray analysis of the surface-treated inorganic filler.

Although a technique which comprises admixing a suitable amount of an organophosphorus compound with a monomer and then admixing the untreated inorganic filler with the resultant mixture to give a resinous composition may be thought to be useful, this technique is undesirable, because it is inferior in filler dispersibility, maximum filler content in the composition, and mechanical strength of the resin product.

In addition, silica-based glass powders containing a metal element such as barium or lanthanum, which are often used in composite resins for dental use, have a large number of silanol groups on their surface. The organophosphorus compound (1) is only poorly effective in the surface treatment of the silanol groups, and hence, it gives unsatisfactory results with the silica-based glass powders. Accordingly, in the case of glass fillers having a high silica content, the combined use of the organophosphorus compound (1) and a known silane coupling agent, such as γ-methacryloyloxypropyl-trimethoxysilane, is preferable.

In this case, a two-step treatment process is employed which involves first performing the surface treatment with the present organophosphorus compounds and then carrying out a further surface treatment using a silane coupling agent.

In a modified process, it is also possible to first carry out the treatment with a silane coupling agent and then the treatment with the present organophosphorus compound, or to perform both treatments in one step using a mixture of the organophosphorus compound (1) and a silane coupling agent.

The monomer capable of radical polymerization to be used in the composition of the present invention should be copolymerizable with the organophosphorus compound (1) used as the surface treating agent, and a (meth)acrylate monomer is used as such monomer. The term "(meth)acrylate" includes, within its meaning a methacrylate and an acrylate.

The composition according to the invention may contain, in addition to said (meth)acrylate monomer, a small proportion of an ester of α-cyanoacrylic, crotonic, cinnamic, sorbic, maleic, itaconic, or the like acid with a mono- or dihydric alcohol, a (meth)acrylamide, such as N-isobutylacrylamide, a vinyl ester, such as vinyl acetate, a vinyl ether, such as butyl vinyl ether, a mono-N-vinyl compound, such as N-vinylpyrrolidone and styrene derivatives.

Examples of the (meth)acrylate monomer are monofunctional (meth)acrylates, such as methyl (meth)acrylate, ethyl (meth)acrylate, lauryl (meth)acrylate, benzyl (meth)acrylate, 2-hydroxyethyl (meth)acrylate and dimethylaminoethyl (meth)acrylate; bifunctional monomers, such as ethylene glycol di(meth)acrylate, triethylene glycol di(meth)acrylate, neopentyl glycol di(meth)acrylate, 1,6-hexanediol di(meth)acrylate, 1,10-decanediol di(meth)acrylate, bisphenol A di(meth)acrylate, 2,2-bis[(meth)acryloyloxypolyethoxyphenyl]propane, 2,2-bis[4-(3-methacryloyloxy-2-hydroxypropoxy)phenyl] propane (hereinafter sometimes referred to as "Bis-GMA") and the adduct of one mole of 2,2,4-trimethylhexamethylene diisocyanate with 2 moles of 2-hydroxyethyl (meth)acrylate; trifunctional monomers, such as trimethylolpropane tri(meth)acrylate; and tetrafunctional monomers, such as pentaerythritol tetra(meth)acrylate and the adduct of one mole of 2,2,4-trimethylhexamethylene diisocyanate with 2 moles of glycerol di(meth)acrylate. These mono- and polyfunctional (meth)acrylates may be used either singly or in the form of a mixture of two or more.

In addition to the above-mentioned monomers, known adhesive monomers may desirably be used in combination, particularly in cases where an adhesiveness to the tooth substance or to dental metals is expected. Such monomers contain an acidic group in their structure. The acidic group here includes, not only in its narrow sense, such groups as

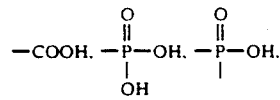
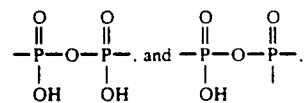

but also in its broad sense, acid anhydride groups such as

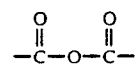

and acid halide groups such as

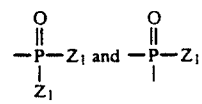

(in which $Z_1$ is F, Cl, Br, or I).

Specific examples of the adhesive monomers are:

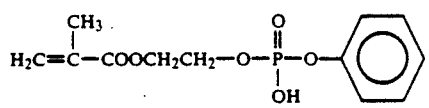

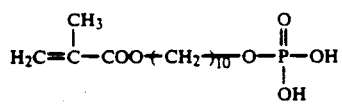

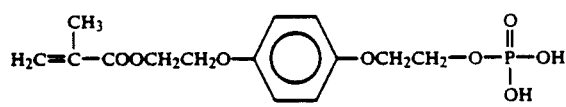

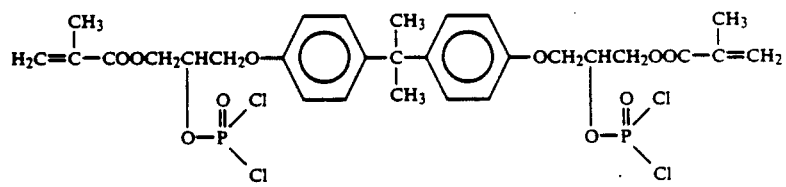

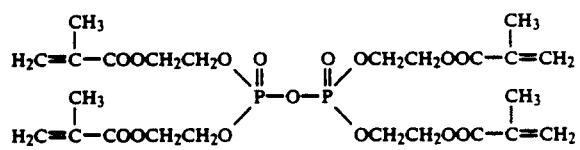

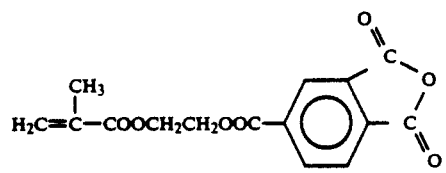

-continued

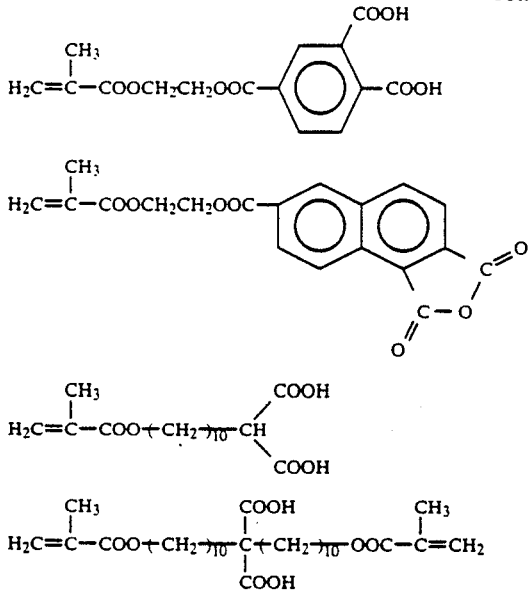

$$\text{H}_2\text{C}=\overset{\text{CH}_3}{\underset{|}{\text{C}}}-\text{COO}-(\text{CH}_2)_{1\text{-}10}-\overset{\text{COOH}}{\underset{\text{COOH}}{\text{CH}}}$$

$$\text{H}_2\text{C}=\overset{\text{CH}_3}{\underset{|}{\text{C}}}-\text{COO}-(\text{CH}_2)_{1\text{-}10}-\overset{\text{COOH}}{\underset{\text{COOH}}{\text{C}}}-(\text{CH}_2)_{1\text{-}10}-\text{OOC}-\overset{\text{CH}_3}{\underset{|}{\text{C}}}=\text{CH}_2$$

The proportion of surface-treated inorganic filler to polymerizable monomer may vary widely depending on the intended use of the resinous composition but, generally, it is within the range of 0.01 to 100 parts by weight of surface-treated inorganic filler per 1 part by weight of polymerizable monomer. A more detailed discussion of the proportion is contained later herein.

The composition of the present invention may further contain, if necessary, one or more other fillers than the inorganic filler. The other fillers may be either of an inorganic nature or of an organic nature and, as inorganic fillers, there may be mentioned, for example, silica-based inorganic fillers such as quartz, amorphous silica and borosilicate glass. These fillers are used after preliminary surface treatment with a silane coupling agent. As organic fillers, there may be mentioned poly(methyl methacrylate), poly(vinyl chloride), polystyrene and other polymer powders as well as such organic-inorganic composite fillers or prepolymerized microfillers as disclosed in Japanese Laid-Open Patent Application Kokai No. 56-49311.

The composition of the present invention, which essentially comprises an inorganic filler and a polymerizable monomer, may be converted to a cured product by subjecting it to heating at a temperature not lower than 100° C. or to irradiation with light or electron beams. Another method to cure the composition is adding an initiator to facilitate the polymerization.

The initiator to be used in the practice of the present invention is not limited to any particular species but may be any of the known initiators. The initiator is generally selected in consideration of the polymerizability of the monomer and the polymerization conditions. Thus, for instance, when a (meth)acrylate is subjected to high-temperature polymerization, an organic peroxide, such as benzoyl peroxide (hereinafter referred to as "BPO"), di-tert-butyl peroxide or cumene hydroperoxide, or an azo compound such as 2,2'-azobisisobutyronitrile or 1,1'-azobis(cyclohexane-1-carbonitrile) is used.

On the other hand, for room temperature polymerization, oxidation-reduction (redox) initiators, such as benzoyl peroxide/dimethylaniline, cumene hydroperoxide/thiourea, ascorbic acid/$Cu^{2+}$ salt, and organic sulfinic acid (or salt thereof)/amine/peroxide, and, further, tributylborane, and organic sulfinic acids are suitably used.

In cases where photopolymerization is carried out by irradiation with visible light, redox initiators, such as $\alpha$-diketone/tertiary amine, $\alpha$-diketone/aldehyde, and $\alpha$-diketone/mercaptan, are preferred. The $\alpha$-diketone is, for example, camphor quinone, diacetyl, 2,3-pentanedione, benzil, acenaphthene quinone or phenanthraquinone. The tertiary amine is, for example, N,N-dimethylaminoethyl methacrylate, ethyl N,N-dimethylaminobenzoate or Michler's ketone. The aldehyde is, for example, citronellal, lauryl aldehyde, o-phthaldialdehyde or p-octyloxybenzaldehyde, and the mercaptan is, for example, 1-decanethiol, thiosalicylic acid, 2-mercaptobenzoxazole or 4-mercaptoacetophenone. Furthermore, an $\alpha$-diketone/organic peroxide/reducing agent initiator system derived from the above-mentioned redox initiator with addition of an organic peroxide is also suitable. For photopolymerization under ultraviolet irradiation, 2,4,6-trimethylbenzoyldiphenylphosphine oxide, benzoin methyl ether, benzil dimethyl ketal, benzophenone, 2-methylthioxanthone, diacetyl, benzil, azobisisobutyronitrile and tetramethylthiuram disulfide are suitably used as well as the above-mentioned initiators for photopolymerization under visible light.

These polymerization initiators are used suitably in an amount within the range of 0.01 to 10% by weight based on the polymerizable monomer.

The resinous composition of the present invention may further contain a polymerization inhibitor, ultraviolet absorber, fluorescent pigment, and pigment if necessary.

The essential components of the resinous composition according to the invention, namely the inorganic filler and polymerizable monomer, can be selected respectively from the above-mentioned substances or compounds so that a wide range of application of said composition can be covered.

In the field of dentistry, the composition according to the invention is required to meet high strength and aesthetic (in particular transparency) requirements so that it can be used as a composite resin for dental application. To meet these requirements, it is recommended that an alumina filler having a refractive index of 1.60 to 1.70, a (meth)acrylate monomer which can give a refractive index of 1.50 to 1.60 after curing by polymerization, and a silica-based inorganic filler having a refractive index of 1.50 to 1.60 be used in combination. The use of such components, which are close in refractive index to one another, can result in good transparency as well as improved mechanical properties owing to the addition of the alumina filler. In this case, the particle size and amount of the fillers can be suitably selected depending on the intended use of the composition.

For use as a dental adhesive intended for adhesion to the tooth, in particular to the dentin, the composition should desirably contain an inorganic filler having good biocompatibility. As such a filler, there may be mentioned, for example, hydroxyapatite, calcium phosphate, calcium hydrogen phosphate, calcium diphosphate, calcium metaphosphate, calcium pyrophosphate, and various kinds of bioglass. It is also possible to use a fluorine-containing inorganic filler, such as calcium fluoride, for the purpose of reinforcing the tooth substance. These fillers are surface-treated with the organophosphorus compound (1).

As the polymerizable monomer component, a system comprising the above-mentioned (meth)acrylate monomer and adhesive monomer is used. The fillers are incorporated in the composition in an amount of 0.5 to 20 parts by weight per one part by weight of the polymerizable monomer component.

When the dental adhesive should serve as a fissure sealant, metal oxides, such as alumina, titanium oxide, and zirconium oxide, and calcium fluoride are preferred inorganic fillers, and these fillers are used in an amount of 0.01 to 5 parts by weight per one part by weight of the polymerizable monomer component.

The resinous composition according to the invention may be formulated in various forms depending on the intended use. Examples are as follows:

(i) One-package paste or liquid form

The filler, polymerizable monomer, and polymerization initiator are combined into a paste or liquid. The initiator is a photopolymerization initiator and/or an initiator for medium or high temperature polymerization.

(ii) Two-package paste or liquid form

The oxidizing agent and reducing agent of an oxidation-reduction type polymerization initiator system capable of catalyzing room temperature polymerization are each separately admixed with either the filler or polymerizable monomer to give two paste or liquid packages.

(iii) Powder-liquid form

This form is composed of a powder which is a mixture of the above-mentioned reducing agent (or oxidizing agent) and a filler powder and a solution (liquid) of the above-mentioned oxidizing agent (or reducing agent) in the polymerizable monomer or monomers.

(iv) Cured article form

The composition in the above-mentioned form (i), to (iii) is molded and cured by polymerization. An artificial tooth is an example of this form.

When offered in the semi-finished forms, (i) to (iii), to dentists or dental technicians, the composition is molded and cured by polymerization by the user and thus, functions as a dental material.

The composite material comprising a metal element-containing, water-insoluble inorganic filler surface-treated in advance with the organophosphorus compound (1) and a monomer capable of radical polymerization is a high performance composition, which has never been attained in the prior art, namely with composite materials in which the above-mentioned inorganic filler or a silica-based filler is treated with a known silane coupling agent. For example, surface modification with silane coupling agents is almost ineffective for metal salt powders, such as calcium carbonate, calcium phosphate and hydroxyapatite and, therefore, composite materials containing these fillers possess poor mechanical strength and cannot be used for dental materials. In contrast, when the organophosphorus compound (1) is used in the surface treatment of metal salts, adhesion between the filler and matrix resin is markedly increased, so that high-strength dental materials can be obtained with metal salts as fillers.

For metal powders as well, the effect of surface modification with silane coupling agents is poor, and, moreover, composite materials containing silane treated metal powders rapidly lose their strength under wet conditions and, therefore, can hardly be employed as dental materials. In contrast, when the organophosphorus compound (1) is used for surface treatment, composite dental materials showing much improved initial strength and wet strength can be obtained.

Surface treatment with the organophosphorus compound (1) is also markedly effective for metal oxide fillers, such as aluminum oxide or titanium oxide fillers, for which surface treatment with silane coupling agents is effective to a considerable extent but does not always give satisfactory water resistance to the resin matrix-filler adhesion. The use of said organophosphorus compound (1) thus makes it possible to incorporate said fillers in composite resins for dental use.

Another outstanding feature of the present invention is that high loading of resin matrices with inorganic fillers is possible. The so-called submicron fillers, which have a particle size of not more than 1 μm, produce a marked viscosity increase and therefore can hardly be incorporated in polymerizable monomers at high concentrations, even after surface treatment with known silane coupling agents.

The difficulty is great, particularly when filler particles are ultrafine, that is having a particle size of not more than 0.1 μm. In contrast, submicron fillers which have been surface-treated with the organophosphorus compound (1), show a low increase of viscosity and can be incorporated into resin matrices in amounts 1.5 to 3 times as large as the inorganic filler treated with a known silane coupling agent. Thus, it is now possible to further improve the hardness, compressive strength, wear resistance, and other aspects of composite resins for dental use.

A further feature of the present invention consists of improved aesthetic features and radiopacity of composite resins for dental use. Since metal, in particular heavy metal, element-containing fillers have great radiopacity, composite resins having a larger radiopacity than enamel can be readily prepared by using these fillers in large amounts.

Furthermore, resinous compositions having a refractive index close to that of natural teeth (n=1.61~1.63) can be obtained by using an inorganic filler which contains a metal element and has a larger refractive index than quartz (n=1.55), and thus, the resinous composition shows improved aesthetic features, e.g., reflection and refraction indexes, comparable to those of natural teeth.

The present invention is applicable to materials for biological hard tissues. More specifically, the invention can be applied to composite resins for dental use (e.g., restorative filling materials; prosthetic materials for inlays, crowns, and the like; materials for artificial teeth; and abutment construction materials) as well as to dental adhesives (e.g., bonding agents, resin cements, and fissure sealants), materials for denture bases, and impression materials, contributing to the improvement of these dental materials.

In the field of orthopedics, the present invention can provide hydroxyapatite-containing bone cement, artificial bone resulting from compounding hydroxyapatite and an organic polymer, and ceramic whisker-reinforced artificial bone.

For industrial purposes, the composition according to the present invention can be used as a material for the manufacture of artificial marble, decorative panels and various machine parts.

Other features of the invention will become apparent in the course of the following descriptions of exemplary embodiments which are given for illustration of the invention and are not intended to be limiting thereof.

EXAMPLES

EXAMPLE 1

A flask was charged with 50 g of alumina (Showa Denko, AL-160 SG-4 ®) having an average particle size of 0.9 μm and a specific surface area of 5.4 m²/g as measured by the Brunauer, Emmett, and Teller (BET) method, 200 ml of toluene and 3 g of 10-methacryloyloxydecyl dihydrogen phosphate, and the mixture was refluxed for 2 hours with vigorous stirring and then allowed to cool. The alumina powder was recovered from the suspension by filtration, washed thoroughly with toluene, dried under vacuum for 12 hours and then heated in air at 90° C. for 2 hours, to give a surface-treated filler. The adsorption of 10-methacryloyloxydecyl dihydrogen phosphate was estimated to be 1.2 parts by weight per 100 parts by weight of the alumina powder based on the phosphorus content determined by fluorescent X-ray analysis, of the powder.

Then, a polymerizable monomer composition was prepared by mixing together 35 parts by weight ob 2,2-bis[methacryloyloxypolyethoxyphenyl]propane (a molecule containing, on an average, 2.6 ethoxy groups; hereinafter referred to as "D-2.6E"), 40 parts by weight of the adduct of one mole of 2,2,4-trimethylhexamethylene diisocyanate and 2 moles of glycerol dimethacrylate (hereinafter referred to as "U-4TH"), 25 parts by weight of neopentyl glycol dimethacrylate (hereinafter referred to as "NPG") and 1 part by weight of benzoyl peroxide. Thirty parts by weight of this composition and 70 parts by weight of the above surface-treated filler were kneaded together to give a pasty polymerizable composition.

This composition was evaluated for the following characteristics:

(i) Consistency

A filler more wettable with a polymerizable monomer will have a better dispersibility in the polymerizable monomer and give a resultant composition lower in viscosity. Therefore, the effect of the surface treatment can be judged by measuring the consistency of the composite as an index of the viscosity. In this experiment, the value measured in the following manner was defined as "consistency". 0.5 ml of the paste was heaped in the middle of a glass plate (5×5 cm). Another glass plate (5×5 cm) was then gently placed thereon under a load of 40 g. After 120 seconds, the major and minor axes of the spread paste body were measured through the upper glass plate. The arithmetic mean of both the values was taken as the consistency. The consistency values shown in Table 1 are the mean of three independent measurements.

(ii) Flexural strength

The flexural strength was measured as an index of the adhesion strength of the filler to the resin matrix in the polymerized composition. The above paste was filled into a 2×2×30 mm mold and cured by heating at 130° C. for 1 hour, and the cured article was then taken out of the mold. The thus-obtained square rod specimen was stored in air at 37° C. for 1 day and then subjected to a three-contact-point flexural test (span between terminal bearing edges=20 mm; cross head speed=1 mm/minute) on an Instron universal tester. The results shown in Table 1 are the mean of 10 measurements (10 test specimens).

(iii) Water resistance in terms of flexural strength

Test specimens, prepared by the method described in the flexural strength test (ii), were subjected to accelerated degradation by immersion in water at 70° C. for 10 days and then tested for flexural strength. The water resistance can be evaluated by comparing the flexural strength after water immersion with the initial flexural strength. The mean value from 10 test specimens is shown in Table 1.

EXAMPLES 2-41

The procedure of Example 1 was followed using the organophosphorus compounds shown in Table 1 in lieu of 10-methacryloyloxydecyl dihydrogen phosphate used in Example 1, and the pastes obtained were evaluated in the same manner as in Example 1. The results are shown in Table 1.

TABLE 1

| No. | Surface-treating agent | Paste consistency (mm) | Flexural strength (kg/cm²) Initial | Flexural strength (kg/cm²) After 10 days in water at 70° C. |
|---|---|---|---|---|
| Example 1 | $H_2C=C(CH_3)-COO+CH_2 \!\!\!\!+_{10}-OP(O)(OH)_2$ | 35 | 1049 | 932 |

TABLE 1-continued

| No. | Surface-treating agent | Paste consistency (mm) | Flexural strength (kg/cm²) Initial | Flexural strength (kg/cm²) After 10 days in water at 70° C. |
|---|---|---|---|---|
| Example 2 | $H_2C=C(CH_3)-COO(CH_2)_3OP(O)(OH)_2$ | 23 | 758 | 606 |
| Example 3 | $H_2C=C(CH_3)-COO(CH_2)_8OP(O)(OH)_2$ | 33 | 1015 | 908 |
| Example 4 | $H_2C=C(CH_3)-COO(CH_2)_{20}OP(O)(OH)_2$ | 40 | 1064 | 961 |
| Example 5 | $H_2C=C(CH_3)-COO(CH_2)_6OP(O)(OH)_2$ | 26 | 783 | 655 |
| Example 6 | $H_2C=C(CH_3)-COO-CH_2-C_6H_4-CH_2O-P(O)(OH)_2$ | 35 | 971 | 816 |
| Example 7 | $H_2C=CH-C_6H_4-(CH_2)_3P(O)(OH)_2$ | 29 | 926 | 832 |
| Example 8 | $H_2C=C(CH_3)-COS(CH_2)_{10}-S-P(O)(OH)_2$ | 34 | 1028 | 915 |
| Example 9 | $H_2C=C(CH_3)-COOCH_2CHCH_2O-C_6H_4-C(CH_3)_2-C_6H_4-OCH_2CHCH_2OOC-C(CH_3)=CH_2$, with $OP(O)(OH)_2$ groups | 31 | 879 | 790 |
| Example 10 | $H_2C=C(CH_3)-COOCH_2CH(C_6H_5)-OP(O)(OH)_2$ | 29 | 892 | 796 |
| Example 11 | $H_2C=C(CH_3)-COO(CH_2)_3CH(CH_2)_3OOC-C(CH_3)=CH_2$, with $OP(O)(OH)_2$ | 30 | 792 | 641 |
| Example 12 | $H_2C=C(CH_3)-CONH(CH_2)_{11}-COO-C[OP(O)(OH)_2]_2$ | 29 | 973 | 892 |
| Example 13 | $H_2C=C(CH_3)-COO(CH_2)_8O-P(O)Cl_2$ | 31 | 1010 | 881 |
| Example 14 | $H_2C=C(CH_3)-COO(CH_2)_{10}O-P(O)Cl_2$ | 32 | 1013 | 896 |
| Example 15 | $H_2C=C(CH_3)-COO(CH_2)_{20}O-P(O)Cl_2$ | 38 | 1065 | 911 |
| Example 16 | $H_2C=C(CH_3)-COO-C_6H_4-C(CH_3)_2-C_6H_4-O-P(O)Cl_2$ | 32 | 892 | 794 |
| Example 17 | $H_2C=C(CH_3)-COOCH_2CHCH_2O-C_6H_4-C(CH_3)_2-C_6H_4-OCH_2CHCH_2-OOC-C(CH_3)=CH_2$, with $OP(O)Cl_2$ groups | 31 | 872 | 763 |

TABLE 1-continued

| No. | Surface-treating agent | Paste consistency (mm) | Flexural strength (kg/cm$^2$) Initial | After 10 days in water at 70° C. |
|---|---|---|---|---|
| Example 18 | $H_2C=\underset{CH_3}{\overset{|}{C}}-COS(CH_2)_{10}-S-P(O)Cl_2$ | 35 | 1001 | 900 |
| Example 19 | $\left[H_2C=\underset{CH_3}{\overset{|}{C}}-COO(CH_2)_3O\right]_2-P(O)OH$ | 24 | 712 | 570 |
| Example 20 | $\left[H_2C=\underset{CH_3}{\overset{|}{C}}-COO(CH_2)_{10}O\right]_2-P(O)OH$ | 37 | 967 | 855 |
| Example 21 | $\left[H_2C=\underset{CH_3}{\overset{|}{C}}-COO(CH_2)_{20}O\right]_2-P(O)OH$ | 43 | 992 | 861 |
| Example 22 | $\left[H_2C=\underset{CH_3}{\overset{|}{C}}-COO(CH_2)_{6}O\right]_2-P(O)OH$ | 26 | 742 | 609 |
| Example 23 | $H_2C=\underset{CH_3}{\overset{|}{C}}-COOCH_2CH_2O-P(O)(OH)O-\text{C}_6\text{H}_5$ | 25 | 725 | 600 |
| Example 24 | $H_2C=\underset{CH_3}{\overset{|}{C}}-COO(CH_2)_{10}-O-P(O)(OH)OCH_3$ | 36 | 901 | 773 |
| Example 25 | $\left[H_2C=\underset{CH_3}{\overset{|}{C}}-COO(CH_2)_{10}O\right]_2-P(O)Cl$ | 36 | 942 | 870 |
| Example 26 | $H_2C=\underset{CH_3}{\overset{|}{C}}-COO-CH_2CH_2-O-P(O)(Cl)O-\text{C}_6\text{H}_5$ | 24 | 700 | 602 |
| Example 27 | (bisphenol-A based bis-methacrylate phosphate chloride structure) | 28 | 842 | 764 |
| Example 28 | $H_2C=\underset{CH_3}{\overset{|}{C}}-COO(CH_2)_{10}-O-P(S)(OH)_2$ | 33 | 1006 | 915 |
| Example 29 | $H_2C=\underset{CH_3}{\overset{|}{C}}-COO(CH_2)_{20}-O-P(S)(OH)_2$ | 39 | 1012 | 940 |
| Example 30 | $H_2C=\underset{CH_3}{\overset{|}{C}}-COO(CH_2)_{10}-O-P(S)(OH)_2$ | 33 | 996 | 935 |
| Example 31 | $H_2C=\underset{CH_3}{\overset{|}{C}}-COO(CH_2)_{10}-O-P(S)Cl_2$ | 32 | 982 | 924 |

TABLE 1-continued

| No. | Surface-treating agent | Paste consistency (mm) | Flexural strength (kg/cm²) Initial | Flexural strength (kg/cm²) After 10 days in water at 70° C. |
|---|---|---|---|---|
| Example 32 | $\left[ H_2C=\underset{CH_3}{\overset{|}{C}}-COO(CH_2)_{10}-O \right]_2 P(S)OH$ | 34 | 912 | 831 |
| Example 33 | $\left[ H_2C=\underset{CH_3}{\overset{|}{C}}-COO(CH_2)_{10}-O \right]_2 P(S)SH$ | 31 | 876 | 812 |
| Example 34 | $\left[ H_2C=\underset{CH_3}{\overset{|}{C}}-COO(CH_2)_{10}-O \right]_2 P(S)Cl$ | 33 | 904 | 810 |
| Example 35 | $H_2C=\underset{CH_3}{\overset{|}{C}}-COOCH_2CH_2O-P(S)(OH)O-C_6H_5$ | 26 | 705 | 629 |
| Example 36 | $H_2C=\underset{CH_3}{\overset{|}{C}}-COO(CH_2)_{10}-O-P(S)(OH)OCH_3$ | 34 | 883 | 755 |
| Example 37 | $\left[ H_2C=\underset{CH_3}{\overset{|}{C}}-COO(CH_2)_{10}-O-P(O)(OH) \right]_2 O$ | 34 | 971 | 896 |
| Example 38 | $\left[ H_2C=\underset{CH_3}{\overset{|}{C}}-COO(CH_2)_{6}-O-P(O)(OH) \right]_2 O$ | 26 | 731 | 623 |
| Example 39 | $H_2C=\underset{CH_3}{\overset{|}{C}}-COO(CH_2)_{10}-O-\underset{OH}{\overset{O}{\overset{\|}{P}}}-O-\underset{OH}{\overset{O}{\overset{\|}{P}}}-OCH_3$ | 35 | 915 | 822 |
| Example 40 | $\left[ H_2C=\underset{CH_3}{\overset{|}{C}}-COO(CH_2)_{10}-O-P(O)(Cl) \right]_2 O$ | 34 | 950 | 866 |
| Example 41 | $\left[ H_2C=\underset{CH_3}{\overset{|}{C}}-COO(CH_2)_{10}-O-P(S)(Cl) \right]_2 O$ | 33 | 967 | 892 |

COMPARATIVE EXAMPLE 1

A paste was prepared by using the same alumina powder as used in Example 1 but without any surface treatment, and the consistency and flexural strength measurements were made in the same manner as in Example 1. The results are shown in Table 2.

COMPARATIVE EXAMPLES 2-5

The same evaluations as made in Example 1 were performed using the alumina powder surface-treated with one of the organophosphorus compounds shown in Table 2 in lieu of the organophosphorus compound used in Example 1. The results thus obtained are shown also in Table 2.

COMPARATIVE EXAMPLE 6

A paste was prepared by adding 69.17 parts by weight of the same alumina powder as used in Example 1, without surface treatment, to a mixture of 30 parts by weight of the same polymerizable monomer composition as used in Example 1 and 0.83 part by weight of 10-methacryloyloxydecyl dihydrogen phosphate, followed by kneading, and consistency and flexural strength measurements were performed in the same manner as in Example 1. The results obtained are shown in Table 2. As compared with the product obtained in Example 1, the product in this comparative example showed a marked decrease in flexural strength.

TABLE 2

| No. | Surface-treating agent | Paste consistency (mm) | Flexural strength (kg/cm²) Initial | Flexural strength (kg/cm²) After 10 day in water at 70° C. |
|---|---|---|---|---|
| Comparative Example | | | | |
| 1 | None | 11 | 530 | 390 |
| 2 | $H_2C=\overset{CH_3}{\underset{|}{C}}-COOCH_2CH_2-O-P(O)(OH)_2$ | 15 | 560 | 500 |
| 3 | $H_2C=\overset{CH_3}{\underset{|}{C}}-COO(CH_2CH_2O)_4-P(O)(OH)_2$ | 20 | 610 | 510 |
| 4 | $H_2C=\overset{CH_3}{\underset{|}{C}}-COOCHClCH(CH_3)-O-P(O)(OH)_2$ | 16 | 550 | 490 |
| 5 | $[H_2C=\overset{CH_3}{\underset{|}{C}}-COOCH_2CH_2-O]_2-P(O)OH$ | 16 | 600 | 480 |
| 6 | None | 27 | 814 | 583 |

EXAMPLES 42-50

A mixture of 40 g of powdery titanium oxide (of the rutile structure; average particle size = 0.2 μm), 400 ml of toluene and 4 g of one of the organophosphorus compounds shown in Table 3 was heated under reflux for 2 hours and then allowed to cool. The titanium oxide powder was filtered off, washed with toluene, dried under vacuum and subjected to a dry heat treatment at 90° C. for 2 hours to give a surface-treated filler.

A paste was prepared by mixing and kneading together 50 parts by weight of the same polymerizable monomer composition as used in Example 1 and 50 parts by weight of the above filler. This paste was subjected to consistency and flexural strength measurements in the same manner as in Example 1. The results obtained are shown in Table 3.

COMPARATIVE EXAMPLES 7-11

Pastes were prepared as in Example 42 using a surface-treated filler prepared by treatment of the above-mentioned titanium oxide powder with one of the organophosphorus compounds shown in Table 3 or using said titanium oxide powder without any surface treatment. Consistency and flexural strength measurements were made in the same manner as in Example 1. The results obtained are shown in Table 3.

TABLE 3

| No. | Surface-treating agent | Paste consistency (mm) | Flexural strength (kg/cm²) Initial | Flexural strength (kg/cm²) After 10 days in water at 70° C. |
|---|---|---|---|---|
| Example | | | | |
| 42 | $H_2C=\overset{CH_3}{\underset{|}{C}}-COO(CH_2)_4-O-P(O)(OH)_2$ | 24 | 648 | 556 |
| 43 | $H_2C=\overset{CH_3}{\underset{|}{C}}-COO(CH_2)_8-O-P(O)(OH)_2$ | 41 | 839 | 773 |
| 44 | $H_2C=\overset{CH_3}{\underset{|}{C}}-COO(CH_2)_{10}-O-P(O)(OH)_2$ | 45 | 860 | 810 |
| 45 | $H_2C=\overset{CH_3}{\underset{|}{C}}-COO(CH_2)_{20}-O-P(O)(OH)_2$ | 45 | 875 | 834 |
| 46 | $H_2C=\overset{CH_3}{\underset{|}{C}}-COO(CH_2)_{76}O-P(O)(OH)_2$ | 32 | 672 | 594 |
| 47 | $H_2C=\overset{CH_3}{\underset{|}{C}}-COOCH_2CH_2-O-P(O)(OH)-O-C_6H_5$ | 25 | 644 | 581 |
| 48 | $H_2C=\overset{CH_3}{\underset{|}{C}}-COO(CH_2)_{10}-O-P(O)(Cl)_2$ | 38 | 825 | 762 |

TABLE 3-continued

| No. | Surface-treating agent | Paste consistency (mm) | Flexural strength (kg/cm$^2$) Initial | Flexural strength (kg/cm$^2$) After 10 days in water at 70° C. |
|---|---|---|---|---|
| 49 | $[H_2C=C(CH_3)-COO(CH_2)_{10}-O]_2-P(S)(OH)$ | 40 | 793 | 699 |
| 50 | $[H_2C=C(CH_3)-COO(CH_2)_{10}-O-P(O)(OH)]_2-O$ | 39 | 832 | 765 |
| Comparative Example | | | | |
| 7 | $H_2C=C(CH_3)-COOCH_2CH_2-O-P(O)(OH)_2$ | 18 | 512 | 435 |
| 8 | $H_2C=C(CH_3)-COO(CH_2CH_2O)_7P(O)(OH)_2$ | 19 | 591 | 458 |
| 9 | $H_2C=C(CH_3)-COOCHClCH(CH_3)-O-P(O)(OH)_2$ | 19 | 588 | 452 |
| 10 | $[H_2C=C(CH_3)-COOCH_2CH_2-O]_2-P(O)OH$ | 20 | 524 | 447 |
| 11 | None | 15 | 503 | 391 |

EXAMPLES 51-59

50 g of a hydroxyapatite powder (average particle size = 75 μm) was admixed with 150 ml of toluene and 1 g of one of the organophosphorus compounds shown in Table 4 and surface-treated by following the procedure of Example 1. A paste was prepared by mixing and kneading together 80 parts by weight of this filler and 20 parts by weight of the same polymerizable monomer composition as used in Example 1. The paste was subjected to the same consistency and flexural strength measurements as performed in Example 1. The results obtained are shown in Table 4.

COMPARATIVE EXAMPLES 12-16

Pastes were prepared as in Example 51 using a filler prepared by surface treatment of the above-mentioned hydroxyapatite powder with one of the organophosphorus compounds shown in Table 4 or using said powder without any surface treatment. The pastes were subjected to the same consistency and flexural strength measurements as performed in Example 1. The results are shown in Table 4.

TABLE 4

| No. | Surface-treating agent | Paste consistency (mm) | Flexural strength (kg/cm$^2$) Initial | Flexural strength (kg/cm$^2$) After 10 days in water at 70° C. |
|---|---|---|---|---|
| Example | | | | |
| 51 | $H_2C=C(CH_3)-COO(CH_2)_4-O-P(O)(OH)_2$ | 25 | 471 | 352 |
| 52 | $H_2C=C(CH_3)-COO(CH_2)_7O-P(O)(OH)_2$ | 36 | 539 | 442 |
| 53 | $H_2C=C(CH_3)-COO(CH_2)_{10}-O-P(O)(OH)_2$ | 38 | 560 | 450 |
| 54 | $H_2C=C(CH_3)-COO(CH_2)_{20}-O-P(O)(OH)_2$ | 40 | 606 | 557 |
| 55 | $[H_2C=C(CH_3)-COO(CH_2)_{10}-O]_2-P(O)OH$ | 41 | 533 | 414 |

TABLE 4-continued

| No. | Surface-treating agent | Paste consistency (mm) | Flexural strength (kg/cm²) Initial | Flexural strength (kg/cm²) After 10 days in water at 70° C. |
|---|---|---|---|---|
| 56 | $H_2C=C(CH_3)-COOCH_2CH_2-O-P(O)(OH)O-C_6H_5$ | 29 | 497 | 380 |
| 57 | $H_2C=C(CH_3)-COO(CH_2)_{10}-O-P(O)Cl_2$ | 35 | 556 | 439 |
| 58 | $[H_2C=C(CH_3)-COO(CH_2)_{10}-O-]_2P(S)OH$ | 36 | 515 | 412 |
| 59 | $[H_2C=C(CH_3)-COO(CH_2)_{10}-O-P(O)(OH)-]_2O$ | 37 | 550 | 422 |
| Comparative Example 12 | $H_2C=C(CH_3)-COOCH_2CH_2-O-P(O)(OH)_2$ | 17 | 392 | 283 |
| 13 | $[H_2C=C(CH_3)-COOCH_2CH_2-O-]_2P(O)(OH)$ | 20 | 400 | 260 |
| 14 | $H_2C=C(CH_3)-COO(CH_2CH_2O)_4-O-P(O)(OH)_2$ | 19 | 420 | 285 |
| 15 | $H_2C=C(CH_3)-COOCHClCH(CH_3)-O-P(O)(OH)_2$ | 21 | 405 | 274 |
| 16 | None | 12 | 359 | 218 |

EXAMPLE 60–63

A flask was charged with 50 g of a silver powder (particle size ≦50 μm), 100 ml of toluene and 0.5 g of one of the organophosphorus compounds shown in Table 5 and then the procedure of Example 1 was followed to give a surface-treated filler. A paste was prepared by mixing and kneading together 93 parts by weight of the filler and 7 parts by weight of the same polymerizable monomer composition as used in Example 1. The paste was subjected to the same consistency and flexural strength measurements as performed in Example 1. The results are shown in Table 5.

COMPARATIVE EXAMPLES 17 and 18

Pastes were prepared as in Example 60 using a filler prepared by surface treatment of the above-mentioned silver powder with one of the organophosphorus compounds shown in Table 5 or using said powder without any surface treatment. The pastes were subjected to the same consistency and flexural strength measurements as performed in Example 1. The results are shown in Table 5.

TABLE 5

| No. | Surface-treating agent | Paste consistency (mm) | Flexural strength (kg/cm²) Initial | Flexural strength (kg/cm²) After 10 days in water at 70° C. |
|---|---|---|---|---|
| Example 60 | $H_2C=C(CH_3)-COO(CH_2)_{10}-O-P(O)(OH)_2$ | 35 | 924 | 784 |
| 61 | $H_2C=C(CH_3)-COO(CH_2)_{10}-O-P(S)(OH)_2$ | 43 | 1015 | 978 |

TABLE 5-continued

| No. | Surface-treating agent | Paste consistency (mm) | Flexural strength (kg/cm$^2$) | |
|---|---|---|---|---|
| | | | Initial | After 10 days in water at 70° C. |
| 62 | $\left[ H_2C=\overset{CH_3}{\underset{|}{C}}-COO+CH_2\overset{}{)_{10}}-O\right]_2 P(S)OH$ | 43 | 991 | 964 |
| 63 | $\left[ H_2C=\overset{CH_3}{\underset{|}{C}}-COO+CH_2\overset{}{)_{10}}-O\right]_2 P(S)SH$ | 46 | 1125 | 1046 |
| Comparative Example | | | | |
| 17 | $H_2C=\overset{CH_3}{\underset{|}{C}}-COOCH_2CH_2-O-P(O)(OH)_2$ | 21 | 621 | 286 |
| 18 | None | 15 | 305 | 171 |

EXAMPLE 64

A La glass ceramic (Schott,, GM-31684 ®; n=1.56) was ground in a vibrating ball mill to give a powder having a particle size range of 0.1 to 20 μm and an average particle size of 2.8 μm. This powder was surface-treated in the conventional manner with γ-methacryloyloxypropyltrimethoxysilane, which was used in an amount of 2 parts by weight per 100 parts by weight of said powder, to give a surface treated filler. Separately, a mixture of 50 g of microfine alumina (Nippon Aerosil, aluminum oxide C ®) having an average particle size of 0.02 μm, a specific surface area of 100 m$^2$/g, as measured by the BET method, and a refractive index of n=1.65, 15 g of 10-methacryloyloxydecyl dihydrogen phosphate and 500 ml of toluene was heated under reflux for 3 hours and then allowed to cool. The filler was recovered by centrifugation, dried under vacuum for 24 hours and then further heated in air at 90° C. for 2 hours to give a surface-treated microfine alumina powder filler. Elemental analysis of this alumina powder revealed an ash content of 85.5% by weight. The same polymerizable monomer composition (n=1.528) as used in Example 1 was used as the polymerizable monomer component except that 0.5 part by weight of 2,4,6-trimethylbenzoyldiphenylphosphine oxide was added per 100 parts by weight of said composition in lieu of BPO.

A polymerizable composition (paste) was prepared by mixing and kneading together 500 parts by weight of the above surface-treated La glass filler, 180 parts by weight of the surface-treated microfine alumina filler and 100 parts by weight of the polymerizable monomer composition, followed by deaeration under vacuum. This paste was polymerized by curing by a 90-second exposure to photoirradiation using a xenon lamp (Kulzer, Dentacolor XS ®), followed by heating for 30 minutes, at 120° C. The thus-obtained cured product was measured for flexural strength, compressive strength, Brinell hardness and transparency. The results obtained are shown in Table 6.

The definitions of the measured quantities and the methods of measurement as used in this example are as follows:

(i) Flexural strength

The same mold as used in Example 1 was employed and polymerization was carried out in the same manner as described above. The thus-obtained moldings were immersed in water at 37° C. for 24 hours and then subjected to three-contact-point flexural testing using an Instron universal tester (cross head speed: 1 mm/minute; span between bearing edges: 20 mm). The value is the mean from 10 test specimens.

(ii) Compressive strength

The paste was filled into a cylindrical mold, 4 mm in diameter and 4 mm in height, and polymerized as described above. The molded article was taken out of the mold, immersed in water at 37° C. for 24 hours and then tested on an Instron universal tester at a cross head speed of 2 mm/minute. The value reported is the mean from 10 test specimens.

(iii) Brinell hardness

The paste was filled into a mold having a diameter of 10 mm and a thickness of 5 mm, a cover glass was brought into contact with the upper surface of the paste under pressure, and polymerization was carried out as described above.

The cured product was taken out of the mold, and the face that had been kept in contact with the glass was polished with an abrasive paper with 220 grit to a depth of 0.5 mm and subjected to testing.

(iv) Transparency

The paste was molded into a disk (20 mm φ×0.85 mm) and, after curing as described above, the molding was used as a test specimen. For the transparency evaluation, a colorimeter (Nippon Denshoku model Σ80) was used, the lightness ($L_1$) was measured with a standard white plate located behind the test specimen on one hand and, on the other, the lightness ($L_2$) was measured with a standard black plate placed behind the same test specimen. The difference, $\Delta L = L_1 - L_2$, was used as an index of transparency. A greater $\Delta L$ value means a higher level of transparency.

(v) Refractive index

The refractive indices of the alumina and inorganic fillers were measured with an Abbe refractometer by the immersion method in a solvent of sulfur-containing diiodomethane, bromonaphthalene, methyl salicylate, or dimethylformamide and using the D line of a sodium lamp as a light source. The refractive index of the polymerizable monomer composition after curing was measured with an Abbe refractometer using, as the test specimen, a cured rectangular parallelepiped molding (5 mm × 10 mm × 20 mm) prepared by deaerating the polymerizable monomer composition containing 0.5% by weight of benzoyl peroxide and then polymerizing the same at 110° C. for 30 minutes.

(vi) Average particle size and particle size range

For the microfine alumina powder, the particle size was determined based on a transmission electron photomicrograph.

For the La glass ceramic, a Horiba model CAPA 500 particle size autoanalyzer was used. The measurement was made with the centrifugal and gravitational sedimentation-light transmission technique.

EXAMPLE 65

A cured product obtained by photopolymerization of the same paste used in Example 64, but without heating, was tested in the same manner as in the same Example. The results are also shown in Table 6.

COMPARATIVE EXAMPLE 19

An alumina filler was prepared by surface-treating 100 parts by weight of the same microfine alumina powder as used in Example 64 with 30 parts by weight of γ-methacryloyloxypropyltrimethoxysilane in the conventional manner. An attempt was made to prepare a composition using this alumina filler and the same La glass ceramic and polymerizable monomer composition as used in Example 64 with the same compounding ratio. However, the viscosity was so high that kneading was impossible.

COMPARATIVE EXAMPLE 20

A microfine silica filler was prepared by surface-treating 100 parts by weight of a microfine silica powder (Nippon Aerosil, Aerosil 130 ®: average particle size 0.016 μm; BET specific surface area 130 m²/g) with 30 parts by weight of γ-methacryloyloxypropyltrimethoxysilane in the conventional manner. An attempt was made to prepare a composition using the microfine silica filler in lieu of the microfine alumina filler used in Example 64, together with the same La glass ceramic and polymerizable monomer composition in the same compounding ratio as used in Example 64. However, the viscosity was so high that kneading was impossible.

COMPARATIVE EXAMPLE 21

A microfine silica filler was prepared by surface-treating 100 parts by weight of a microfine silica powder (Nippon Aerosil, Aerosil OX-50 ®; average particle size 0.04 μm; BET specific surface area 50 m²/g) with 15 parts by weight of γ-methacryloyloxypropyltrimethoxysilane in the conventional manner. Said silica filler was mixed and kneaded with the same La glass ceramic and polymerizable monomer composition as used in Example 64 in the same compounding ratio as used therein, the silica filler being used in lieu of the microfine alumina filler. The resultant composition was cured by the same polymerization method used in Example 64, and test specimens thus-obtained were subjected to the same tests described above. The results are shown in Table 6.

EXAMPLE 66

A polymerizable monomer composition was prepared by mixing together 40 parts by weight of D-2.6E, 40 parts by weight of 1,10-decanediol dimethacrylate, 20 parts by weight of U-4TH and 1 part by weight of benzoyl peroxide (BPO). A polymerizable composition in the form of a paste was prepared by mixing and kneading together 100 parts by weight of this polymerizable monomer composition and 250 parts by weight of the same microfine alumina filler used in Example 64. This paste was cured by heating at 130° C. for 1 hour to effect polymerization, and the cured product was tested in the same manner as in Example 64. The test results are also shown in Table 6.

COMPARATIVE EXAMPLE 22

250 parts by weight of the same surface-treated alumina filler used in Example 19 were mixed with 100 parts by weight of the same polymerizable monomer composition used in Example 66. However, the mixture did not give a paste suited for use as a dental material; kneading was impossible.

COMPARATIVE EXAMPLE 23

The procedure of Example 66 was followed except for using 200 parts by weight of the same microfine silica filler used in Comparative Example 21 and 100 parts by weight of the same polymerizable monomer composition used in Example 66. The evaluation results are shown in Table 6.

EXAMPLE 67

The cured product produced in Example 66 was ground in a vibrating ball mill and then sifted to give a powder having a particle size range of 0.1 μm to 100 μm and an average particle size of 15 μm. Separately, a polymerizable monomer composition was prepared by mixing together 70 parts by weight of D-2.6E, 30 parts by weight of 1,6-hexanediol dimethacrylate and 0.5 part by weight of 2,4,6-trimethylbenzoyldiphenylphosphine oxide. A polymerizable composition was prepared by mixing and kneading together 20 parts by weight of said monomer composition, 55 parts by weight of the above-described powder and 25 parts by weight of the same microfine alumina filler used in Example 64. The cured product obtained from this composition by the same polymerization method used in Example 64 was tested in the same manner. The results are shown in Table 6.

COMPARATIVE EXAMPLE 24

The cured product produced in Comparative Example 23 was ground in a vibrating ball mill and then sifted to give a powder having a particle size range of 0.1 μm to 100 μm and an average particle size of 14 μm.

A polymerizable composition was prepared by mixing and kneading together 20 parts by weight of the same polymerizable monomer composition used in Example 67, 55 parts by weight of the this powder, and 25 parts by weight of the same microfine silica filler used in Comparative Example 21. The same evaluation tests performed in Example 67 were carried out, and the results are shown in Table 6.

TABLE 6

|  | Example 64 | Comparative Example 21 | Example 65 | Example 66 | Comparative Example 23 | Example 67 | Comparative Example 24 |
| --- | --- | --- | --- | --- | --- | --- | --- |
| Flexural strength (kg/cm$^2$) | 1650 | 1250 | 1510 | 880 | 650 | 1020 | 860 |
| Compressive strength (kg/cm$^2$) | 5910 | 3920 | 4690 | 4350 | 3760 | 4600 | 3970 |
| Brinell hardness | 88 | 70 | 71 | 48 | 40 | 45 | 38 |
| Transparency ΔL | 38 | 8 | 38 | 45 | 43 | 43 | 22 |

EXAMPLE 68

The same hydroxyapatite powder used in Example 51 was ground in a rotary ball mill to give a powder having an average particle size of 4.5 μm. 50 g of this powder was mixed with 150 ml of toluene and 1.5 g of 10-methacryloyloxydecyl dihydrogen phosphate, and surface treatment was carried out by following the procedure of Example 1. A two-package adhesive (liquid and powder) was prepared using the thus-obtained filler and according to the following formulation;

| Composition A (liquid) | |
| --- | --- |
| D-2.6E | 50 parts by weight |
| NPG | 25 parts by weight |
| 2-Hydroxyethyl methacrylate | 10 parts by weight |
| 10-methacryloyloxydecyl dihydrogen phosphate | 15 parts by weight |
| Benzoyl peroxide | 1 part by weight |
| Hydroquinone monomethyl ether | 0.05 part by weight |
| Composition B (powder) | |
| Surface-treated hydroxyapatite filler mentioned above | 100 parts by weight |
| Sodium benzenesulfinate | 0.3 part by weight |
| N,N-Diethanol-p-toluidine | 0.3 part by weight |

In preparing composition B, the filler was sprayed with a solution of the sodium benzenesulfinate and N,N-diethanol-p-toluidine in 10 parts by weight of methanol, and then the methanol was evaporated.

A test for adhesion to human dentin was conducted using compositions A and B. The dentin of a human molar was exposed by cutting the crown portion off with a cutter while pouring water thereonto. The dentin surface was etched with 40% aqueous orthophosphoric acid for 1 minute, washed with water and then dried with an air syringe. A double adhesive tape piece having a 5 mm φ perforation was then applied to said surface. The tooth was fixed horizontally, and a plastic ring (6 mm in inside diameter, 5 mm in height) was placed concentrically on the perforation of the tape. Appropriate quantities of compositions A and B were kneaded together in the weight ratio of 1:4 for about 1 minute and, when the mixture became a soft paste, the paste was put into the plastic ring, then a hook for tensile testing was set in the paste, and the specimen was allowed to stand for 30 minutes and then immersed in water at 37° C. for 24 hours. Thereafter, the adhesive strength was measured using an Instron universal tester at a cross head speed of 2 mm/minute. The value is a mean of 5 test specimens. The initial flexural strength of this cured product and the flexural strength after 10 days of immersion in water at 70° C. were also measured. The results of these measurements are shown in Table 7.

COMPARATIVE EXAMPLE 25

An adhesive was prepared according to the same formulation as given in Example 68 except that γ-methacryloyloxypropyltrimethoxysilane was used as the surface-treating agent in lieu of the 10-methacryloyloxydecyl dihydrogen phosphate used in Example 68, and the surface treatment was performed in the conventional manner. The adhesive was tested in the same manner as in Example 68. The results are also shown in Table 7.

COMPARATIVE EXAMPLE 26

An adhesive was prepared according to the same formulation as used in Example 68 except that the same hydroxyapatite powder used in Example 51 was used without surface treatment in lieu of the surface-treated hydroxyapatite filler. The adhesive was tested in the same manner, and the results are also shown in Table 7.

TABLE 7

|  | Adhesive strength (kg/cm$^2$) | Flexural strength (kg/cm$^2$) | |
| --- | --- | --- | --- |
|  |  | Initial | After 10 days in water at 70° C. |
| Example 68 | 117 | 928 | 806 |
| Comparative Example 25 | 98 | 853 | 615 |
| Comparative Example 26 | 91 | 864 | 596 |

EXAMPLE 69

The same hydroxyapatite powder used in Example 51 was ground in a vibrating ball mill to give a powder having an average particle size of 2.3 μm. 200g of this powder was mixed with 600 ml of toluene and 10 g of 10-methacryloyloxydecyl dihydrogen phosphate, and surface treatment was carried out as in Example 69. A polymerizable composition was prepared by mixing together 75 parts by weight of the surface-treated filler, 20 parts by weight of methyl methacrylate, 5 parts by weight of 1,10-decanediol dimethacrylate and 0.1 part by weight of benzoyl peroxide. The composition was put into a mold and heated under pressure at 140° C. for 1 hour to effect polymerization. Thus was obtained a molding having biocompatibility and physical properties suitable for use as an artificial tooth root or an artificial bone.

EXAMPLE 70

Three pastes were prepared by adding a coloring agent to the photopolymerizable composition prepared in Example 64 so that they could have the respective chromaticities of the cured products given in Table 8. The color tones match those of tooth neck, dentin, and enamel, respectively. A gold-silver-palladium alloy (GC Corp., Castwell®) was cast into a metal frame suited for use as a crown for a resin facing for the maxillary central incisor. The frame was coated with an opaquer (Kulzer Dentacolor ® opaquer A-20) for masking the metallic color thereof and subjected to photoirradiation for 90 seconds using a xenon lamp (Kulzer Dentacolor XS ®). The paste prepared for tooth neck was applied thereto and photoirradiated for 30 seconds, then the paste for dentin was placed thereon and photoirradiated for 30 seconds, and the paste for enamel was further layered thereon and photoirradiated for 90 seconds. The complete article was placed in a hot air drier and heated at 120° C. for 20 minutes, and then allowed to cool. After trimming and buffing, there was obtained a nice facing crown.

TABLE 8

| No. | a* | b* | L* |
|---|---|---|---|
| 1. (For tooth neck) | 0.08 | 26.82 | 71.50 |
| 2. (For dentin) | −2.28 | 19.98 | 76.20 |
| 3. (For enamel) | −1.01 | 5.45 | 80.03 |

*A disk of cured product, 0.85 mm in thickness and about 20 mm in diameter, was prepared and the chromaticity was measured with a colorimeter (Nippon Denshoku model Σ80) with a standard white plate in the background.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A curable resinous composition, which comprises:
(a) a metal element-containing inorganic filler which has been treated with an oxo acid of pentavalent phosphorus or a derivative thereof, which has the formula:

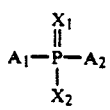

wherein $A_1$ is an organic group having at least one ethylenic double bond capable of radical polymerization and containing 5 to 60 carbon atoms; $A_2$ is a hydroxyl group, a mercapto group, a halogen atom, or an organic group containing 1 to 60 carbon atoms; at least one of $A_1$ and $A_2$ contains at least one hydrocarbyl group containing 4 to 60 carbon atoms, $X_1$ is an oxygen atom or a sulfur atom, and $X_2$ is a hydroxyl group, a mercapto group or a halogen atom; and
(b) at least one monomer capable of radical polymerization which is selected from the group consisting of methacrylates and acrylates.

2. The composition of claim 1, wherein $A_1$ is a univalent organic group of the formula:

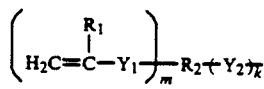

in which $R_1$ is a hydrogen atom or a methyl group, $R_2$ is an organic group which contains 4 to 40 carbon atoms, contains at least one hydrocarbyl group with 4 to 40 carbon atoms, has a valence of (m+1) and is bound to each of the $Y_1$ and $Y_2$ groups with a carbon atom contained therein, $Y_1$ is —COO—, —COS—, or —CONR$_3$—, where $R_3$ is a hydrogen atom or a hydrocarbyl group containing 1 to 6 carbon atoms, $Y_2$ is an oxygen atom, a sulfur atom, or

m is an integer of 1 to 4, and k is an integer of 0 or 1, and wherein $A_2$ is a hydroxyl group, a mercapto group, or a halogen atom.

3. The composition of claim 1, wherein $A_1$ is a univalent organic group of the formula:

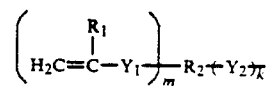

in which $R_1$ is a hydrogen atom or a methyl group, $R_2$ is an organic group which contains 4 to 40 carbon atoms, contains at least one hydrocarbyl group with 4 to 40 carbon atoms, has a valence of (m+1) and is bound to each of the $Y_1$ and $Y_2$ groups with a carbon atom contained therein, $Y_1$ is —COO—, —COS—, —or CONR$_3$—, where $R_3$ is a hydrogen atom or a hydrocarbyl group containing 1 to 6 carbon atoms, $Y_2$ is an oxygen atom, a sulfur atom, or

m is an integer of 1 to 4, and k is an integer of 1 or 1;
and wherein $A_2$ is a univalent organic group of the formula:

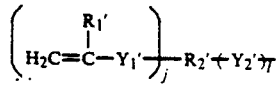

in which $R_1'$ is a hydrogen atom or a methyl group, $R_2'$ is an organic group which contains 1 to 40 carbon atoms, has a valence of (j+1) and is bound to each of the $Y_1'$ and $Y_2'$ groups with a carbon atom contained therein, $Y_1'$ is —COO—, —COS—, or —CONR$_3'$—, where $R_3'$ is a hydrogen atom or a hydrocarbyl group containing 1 to 6 carbon atoms, $Y_2'$ is an oxygen atom, a sulfur atom, or

j is an integer of 0 to 4, and l is an integer of 0 or 1.

4. The composition of claim 1, wherein $A_1$ is a univalent organic group of the formula:

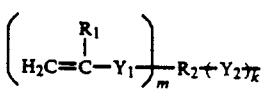

in which $R_1$ is a hydrogen atom or a methyl group, $R_2$ is an organic group which contains 4 to 40 carbon atoms, contains at least one hydrocarbyl group with 4 to 40 carbon atoms, has a valence of (m+1)

and is bound to each of the $Y_1$ and $Y_2$ groups with a carbon atom contained therein, $Y_1$ is —COO—, —COS—, or —CONR$_3$—, where R$_3$ is a hydrogen atom or a hydrocarbyl group containing 1 to 6 carbon atoms. $Y_2$ is an oxygen atom, a sulfur atom, or

m is an integer of 1 to 4, and k is an integer of 0 or 1;

and wherein A$_2$ is a univalent organic group of the formula:

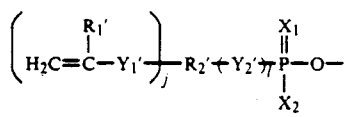

in which R$_1'$ is a hydrogen atom or a methyl group, R$_2'$ is an organic group which contains 1 to 40 carbon atoms, has a valence of (j+1) and is bound to each of the $Y_1'$ and $Y_2'$ groups with a carbon atom contained therein, $Y_1'$ is —COO—, —COS—, or —CONR$_3'$—, where R$_3'$ is a hydrogen atom or a hydrocarbyl group containing 1 to 6 carbon atoms, $Y_2'$ is an oxygen atom, a sulfur atom, or

j is an integer of 0 to 4, and l is an integer of 0 or 1; $X_1$ is an oxygen atom or a sulfur atom; and $X_2$ is a hydroxyl group, a mercapto group, or a halogen atom.

5. The composition of claim 2, wherein $X_1$ is an oxygen atom, and $X_2$ and $A_2$ are each a hydroxyl group.

6. The composition of claim 2, wherein $X_1$ is an oxygen atom, and $X_2$ and $A_2$ are each a chlorine atom.

7. The composition of claim 2, wherein $X_1$ is a sulfur atom.

8. The composition of claim 3, wherein $X_1$ is an oxygen atom and $X_2$ is a hydroxyl group.

9. The composition of claim 3, wherein $X_1$ is an oxygen atom and $X_2$ is a chlorine atom.

10. The composition of claim 3, wherein $X_1$ is a sulfur atom.

11. The composition of claim 2, wherein m is 1 and R$_2$ is a group of the formula:

in which h is an integer of 0 or 1 and, when h is 0, R$_4$ is a hydrocarbyl group containing 4 to 20 carbon atoms and $Y_3$ is an oxygen atom; and when h is 1, R$_4$ is a hydrocarbyl group containing 2 to 9 carbon atoms, R$_5$ is a hydrocarbon residue containing 4 to 20 carbon atoms and $Y_3$ is an oxygen atom, —COO— or —OOC—.

12. The composition of claim 3, wherein m is 1 and R$_2$ is a group of the formula:

in which h is an integer of 0 or 1 and, when h is 0, R$_4$ is a hydrocarbyl group containing 4 to 20 carbon atoms and $Y_3$ is an oxygen atom; and when h is 1, R$_4$ is a hydrocarbyl group containing 2 to 9 carbon atoms, R$_5$ is a hydrocarbon residue containing 4 to 20 carbon atoms and $Y_3$ is an oxygen atom, —COO— or —OOC—.

13. The composition of claim 4, wherein m is 1 and R$_2$ is a group of the formula:

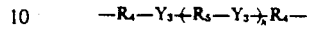

in which h is an integer of 0 or 1 and, when h is 0, R$_4$ is a hydrocarbyl group containing 4 to 20 carbon atoms and $Y_3$ is an oxygen atom; and when h is 1, R$_4$ is a hydrocarbyl group containing 2 to 9 carbon atoms, R$_5$ is a hydrocarbon residue containing 4 to 20 carbon atoms and $Y_3$ is an oxygen atom, —COO— or —OOC—.

14. The composition of claim 2, wherein m is 1 and R$_2$ is a group of the general formula:

in which i is an integer of 4 to 40.

15. The composition of claim 3, wherein m is 1 and R$_2$ is a group of the general formula:

in which i is an integer of 4 to 40.

16. The composition of claim 4, wherein m is 1 and R$_2$ is a group of the general formula:

in which i is an integer of 4 to 40.

17. A cured article, prepared by curing a curable resinous compositon, which comprises:
(a) a metal element-containing inorganic filler which has been treated with an oxo acid of pentavalent phosphorus or a derivative thereof, which has the formula:

wherein A$_1$ is an organic group having at least one ethylenic double bond capable of radical polymerization and containing 5 to 60 carbon atoms; A$_2$ is a hydroxyl group, a mercapto group, a halogen atom, or an organic group containing 1 to 60 carbon atoms; at least one of A$_1$ and A$_2$ contains at least one hydrocarbyl group containing 4 to 60 carbon atoms, X$_1$ is an oxygen atom or a sulfur atom, and X$_2$ is a hydroxyl group, a mercapto group or a halogen atom; and (b) at least one monomer capable of radical polymerization which is selected from the group consisting of methacrylates and acrylates.

18. The composition of claim 1, wherein said metal element-containing inorganic filler which has been treated with said oxo acid of pentavalent phosphorus is prepared by a process comprising:

(i) suspending said inorganic filler and said oxo acid of pentavalent phosphorus in a solvent selected from the group consisting of water, alcohol, hexane, benzene, toluene, and xylene, to obtain a suspension;

(ii) stirring said suspension; and (iii) removing said solvent from said suspension.

19. The composition of claim 1, wherein said metal element-containing inorganic filler which has been treated with said oxo acid of pentavalent phosphorus is prepared by a process comprising:

(i) charging said inorganic filler into a mixer; and (ii) adding said oxo acid of pentavalent phosphorus to said mixer while stirring.

* * * * *

UNITED STATES PATENT AND TRADEMARK OFFICE
CERTIFICATE OF CORRECTION

PATENT NO. : 5,055,497
DATED : October 8, 1991
INVENTOR(S) : Koichi Okada et al

It is certified that error appears in the above-indentified patent and that said Letters Patent is hereby corrected as shown below:

Col. 4, line 42, delete "$K_2O.TiO_2$, $BaO.TiO_2$, $CaO.Al_2O_2$ and insert --$K_2O\ TiO_2$, $BaO\ TiO_2$, $CaO\ Al_2O_2$,--.
Col. 4, line 45, delete "Shott" and insert --Schott--.
Col. 4, line 46, delete "Shott" and insert --Schott--.
Col. 4, line 47, delete "Shott" and insert --Schott--.
Col. 4, line 49, delete "Shott" and insert --Schott--.
Col. 60, line 23, insert --comparative-- before "Example 19".
Col. 66, line 21, Claim 14, delete "$-CH_2-_i$" and insert -- $\{CH_2\}_i$ --.
Col. 66, line 26, Claim 15, delete "$-CH_2-_i$" and insert -- $\{CH_2\}_i$ --.
Col. 66, line 33, Claim 16, delete "$-CH_2-_i$" and insert -- $\{CH_2\}_i$ --.

Signed and Sealed this

Twentieth Day of September, 1994

Attest:

BRUCE LEHMAN

Attesting Officer

Commissioner of Patents and Trademarks